(12) United States Patent
Iwasaki et al.

(10) Patent No.: US 11,395,629 B2
(45) Date of Patent: Jul. 26, 2022

(54) DETECTION DEVICE FOR PLACEMENT IN CONTACT WITH THE EYE OF A USER

(71) Applicant: Sony Corporation, Tokyo (JP)

(72) Inventors: Masanori Iwasaki, Kanagawa (JP); Ken Hayakawa, Kanagawa (JP); Tsukasa Yoshimura, Tokyo (JP); Masakazu Yajima, Chiba (JP); Naoto Yamaguchi, Tokyo (JP); Akira Tange, Tokyo (JP)

(73) Assignee: Sony Corporation, Tokyo (JP)

( * ) Notice: Subject to any disclaimer, the term of this patent is extended or adjusted under 35 U.S.C. 154(b) by 116 days.

(21) Appl. No.: 15/317,456

(22) PCT Filed: Jun. 8, 2015

(86) PCT No.: PCT/JP2015/002858
§ 371 (c)(1),
(2) Date: Dec. 9, 2016

(87) PCT Pub. No.: WO2015/194120
PCT Pub. Date: Dec. 23, 2015

(65) Prior Publication Data
US 2017/0119311 A1 May 4, 2017

(30) Foreign Application Priority Data

Jun. 18, 2014 (JP) ............... JP2014-125160

(51) Int. Cl.
*G06V 20/59* (2022.01)
*A61B 5/00* (2006.01)
(Continued)

(52) U.S. Cl.
CPC .......... *A61B 5/6821* (2013.01); *A61B 3/0025* (2013.01); *A61B 3/10* (2013.01);
(Continued)

(58) Field of Classification Search
CPC ....... A61B 5/6821; A61B 3/0025; A61B 3/10; A61B 3/113; A61B 5/01; A61B 5/02416;
(Continued)

(56) References Cited

U.S. PATENT DOCUMENTS 5,682,210 A    10/1997   Wirich
5,813,982 A *   9/1998   Baratta ................. A61B 3/165
                                                          374/E13.003
(Continued)

FOREIGN PATENT DOCUMENTS

EP    2609852 A1   7/2013
EP    2772791 A1   9/2014
(Continued)

OTHER PUBLICATIONS

International Search Report and Written Opinion dated Aug. 18, 2015 in connection with International Application No. PCT/JP2015/002858.
(Continued)

*Primary Examiner* — Daniel L Cerioni
(74) *Attorney, Agent, or Firm* — Lock See Yu-Jahnes

(57) ABSTRACT

A device for placement in contact with an eye of a user. The device includes at least one detector for measuring at least one property, and a signal processor for determining, based on the at least one property, whether the eye of the user is closed.

21 Claims, 23 Drawing Sheets

(51) Int. Cl.
   *A61B 3/113* (2006.01)
   *A61B 5/01* (2006.01)
   *G02C 7/04* (2006.01)
   *A61B 5/18* (2006.01)
   *G02C 7/08* (2006.01)
   *G04G 21/00* (2010.01)
   *A61B 3/10* (2006.01)
   *G06V 40/19* (2022.01)
   *A61B 3/00* (2006.01)
   *A61B 5/024* (2006.01)
   *A61B 5/026* (2006.01)
   *A61B 5/11* (2006.01)
   *A61B 5/145* (2006.01)
   *A61H 23/02* (2006.01)
   *A61N 5/06* (2006.01)

(52) U.S. Cl.
   CPC ........... *A61B 3/113* (2013.01); *A61B 5/01* (2013.01); *A61B 5/0261* (2013.01); *A61B 5/02416* (2013.01); *A61B 5/02438* (2013.01); *A61B 5/1116* (2013.01); *A61B 5/14507* (2013.01); *A61B 5/18* (2013.01); *A61B 5/4809* (2013.01); *A61H 23/02* (2013.01); *A61N 5/0613* (2013.01); *G02C 7/04* (2013.01); *G02C 7/083* (2013.01); *G04G 21/00* (2013.01); *G06V 20/597* (2022.01); *G06V 40/19* (2022.01); *A61B 5/024* (2013.01); *A61B 5/026* (2013.01); *A61B 5/1103* (2013.01); *A61B 2560/0242* (2013.01); *A61B 2562/0219* (2013.01)

(58) Field of Classification Search
   CPC . A61B 5/02438; A61B 5/0261; A61B 5/1116; A61B 5/14507; A61B 5/18; A61B 5/4809; A61H 23/02; A61N 5/0613; G02C 7/04; G02C 7/083; G04G 21/00; G06K 9/00604; G06K 9/00845
   USPC ........................................................ 600/587
   See application file for complete search history.

(56) References Cited

U.S. PATENT DOCUMENTS

| | | | |
|---|---|---|---|
| 6,423,001 B1 | 7/2002 | Abreu | |
| 8,608,310 B2 | 12/2013 | Otis et al. | |
| 8,684,946 B1* | 4/2014 | Sims | A61B 3/032 351/246 |
| 2003/0021601 A1 | 1/2003 | Goldstein | |
| 2003/0117369 A1* | 6/2003 | Spitzer | A61B 3/113 345/156 |
| 2004/0019303 A1* | 1/2004 | Thomson | A61B 5/103 600/595 |
| 2008/0137034 A1* | 6/2008 | Wernick | A61B 3/1216 351/221 |
| 2009/0054908 A1* | 2/2009 | Zand | A61B 5/0071 606/130 |
| 2009/0105605 A1* | 4/2009 | Abreu | A61B 5/0008 600/549 |
| 2010/0081943 A1* | 4/2010 | Watson | A61B 5/0059 600/484 |
| 2013/0102857 A1* | 4/2013 | Wolfberg | A61B 5/0444 600/301 |
| 2013/0207889 A1* | 8/2013 | Chang | A61B 5/0002 345/156 |
| 2013/0296977 A1* | 11/2013 | Chiu | A61B 18/18 607/89 |
| 2014/0316310 A1* | 10/2014 | Ackermann | A61N 1/36046 601/46 |
| 2014/0343371 A1* | 11/2014 | Sowers, II | A61B 5/1455 600/301 |
| 2015/0005750 A1* | 1/2015 | Kelleher | A61N 5/0625 606/3 |
| 2015/0277147 A1* | 10/2015 | Kim | G02C 7/04 351/159.02 |
| 2015/0305689 A1* | 10/2015 | Gourmelon | A61B 5/002 600/301 |

FOREIGN PATENT DOCUMENTS

| | | |
|---|---|---|
| JP | 11-249064 A | 9/1999 |
| JP | 2003-076353 A | 3/2003 |
| JP | 2007-127716 A | 5/2007 |
| WO | WO 90/12534 A1 | 11/1990 |
| WO | WO 02/067688 A1 | 9/2002 |
| WO | WO 2013/033349 A1 | 3/2013 |

OTHER PUBLICATIONS

International Preliminary Report on Patentability dated Dec. 29, 2016 in connection with International Application No. PCT/JP2015/002858.

\* cited by examiner

DETECTION DEVICE FOR PLACEMENT IN CONTACT WITH THE EYE OF A USER

CROSS REFERENCE TO RELATED APPLICATIONS

This application claims the benefit under 35 U.S.C. § 371 as a U.S. National Stage Entry of International Application No. PCT/JP2015/002858, filed in the Japanese Patent Office on Jun. 8, 2015, which claims priority to Japanese Priority Patent Application No. JP 2014-125160, filed in the Japanese Patent Office on Jun. 18, 2014, each of which is incorporated by reference herein in its entirety.

TECHNICAL FIELD

The present technology relates to a detection device, a detection method, and a program. In particular, the present technology relates to a detection device, a method, and a program, each of which is capable of detecting opening and closing of an eyelid of a user using a simpler configuration.

BACKGROUND ART

In the related art, there is an existing display device which may be mounted to a user, such as a head mounted display or a contact lens type display device. In such a display device, if the opening and closing of the eyelid of the user is detected or the like, and it is determined whether the user is in a conscious state or in a sleeping state, it is possible to perform more appropriate drive control.

For example, separate from a video display unit which is mounted on the underside of an eyelid, technology in which a detection unit is provided on the surface of the eyelid, and the opening and closing of the eyelid is detected by the detection unit based on a weak electrical signal which is generated by movement of the eyelid is proposed as the technology for detecting the opening and closing of the eyelid (for example, refer to PTL 1). In this technology, the opening and closing of the eyelid of the user is detected from a difference between an electrical signal which is generated from muscles in a state in which the eyelid is open, and an electrical signal which is generated from the muscles in a state in which the eyelid is closed.

For example, technology in which the opening and closing of the eyelid is detected by providing a light source which irradiates an eye of the user with infrared light, and a light reception unit which detects the infrared light that is reflected from the eye is proposed (for example, refer to PTL 2). In this technology, when the eyelid of the user is open, since the infrared light is reflected by the eyeball, which has a smooth surface, a strong reflected light is obtained; however, when the eyelid is closed, since most of the infrared light is absorbed by the skin of the eyelid, the reflected light becomes weak, and this fact is used.

For example, there is also technology in which, by providing a camera which captures the eye of the user and analyzing an image of the eye that is captured by the camera, the opening and closing of the eyelid is detected (for example, refer to PTL 3). In this technology, when the eyelid is open, the contrast difference between the white, the iris, and the pupil of the eyeball is obtained, and, when the eyelid is closed, the skin portion of the eyelid has little contrast, and this fact is used to determine the opening and closing of the eyelid of the user.

CITATION LIST

Patent Literature

PTL 1: Japanese Unexamined Patent Application Publication No. 2007-127716
PTL 2: Japanese Unexamined Patent Application Publication No. H11-249064
PTL 3: Japanese Unexamined Patent Application Publication No. 2003-076353

SUMMARY OF INVENTION

Technical Problem

However, it is difficult to detect the opening and closing of the eyelid using a simple configuration in the technologies described above.

For example, in the technology which detects the opening and closing of the eyelid by using weak electrical signals which are generated from the muscles, since a detection unit has to be mounted on the surface of the eyelid separately from the video display unit, the usability is degraded. The electrical signal which is generated by the muscles is weak, and it is difficult to detect the opening and closing of the eyelid with high precision.

Even in the technology in which the light source which radiates infrared light, and the light reception unit which detects the infrared light that is reflected are provided, an external detection device, which is separate from the display device, is necessary, and the usability is degraded. Similarly, even in the technology that analyzes an image of an eye that is captured by a camera, an external device such as a camera is necessary.

In particular, since the contact lens type display device is mounted to the eyeball of the user and used wirelessly, using an external device in the detection of the opening and closing of the eyelid causes the user to carry or to mount excessive equipment, and this is a burden. Therefore, it is necessary to detect the opening and closing of the eyelid using a simpler configuration.

It is desirable to detect the opening and closing of an eyelid of a user using a simpler configuration.

Solution to Problem

Some embodiments relate to a device for placement in contact with an eye of a user. The device includes at least one detector configured to measure at least one property, and a signal processor configured to determine, based on the at least one property, whether the eye of the user is closed.

Other embodiments are directed to a device for placement in contact with an eye of a user, the device including a temperature detector configured to detect a temperature outside the device and/or a temperature of the eye of the user.

Advantageous Effects of Invention

According to the embodiments of the present technology, it is possible to detect the opening and closing of an eyelid of a user using a simpler configuration.

Note that, the effects described herein are not limited, and may be any of the effects described in the present disclosure.

DESCRIPTION OF EMBODIMENTS

Figure 1:
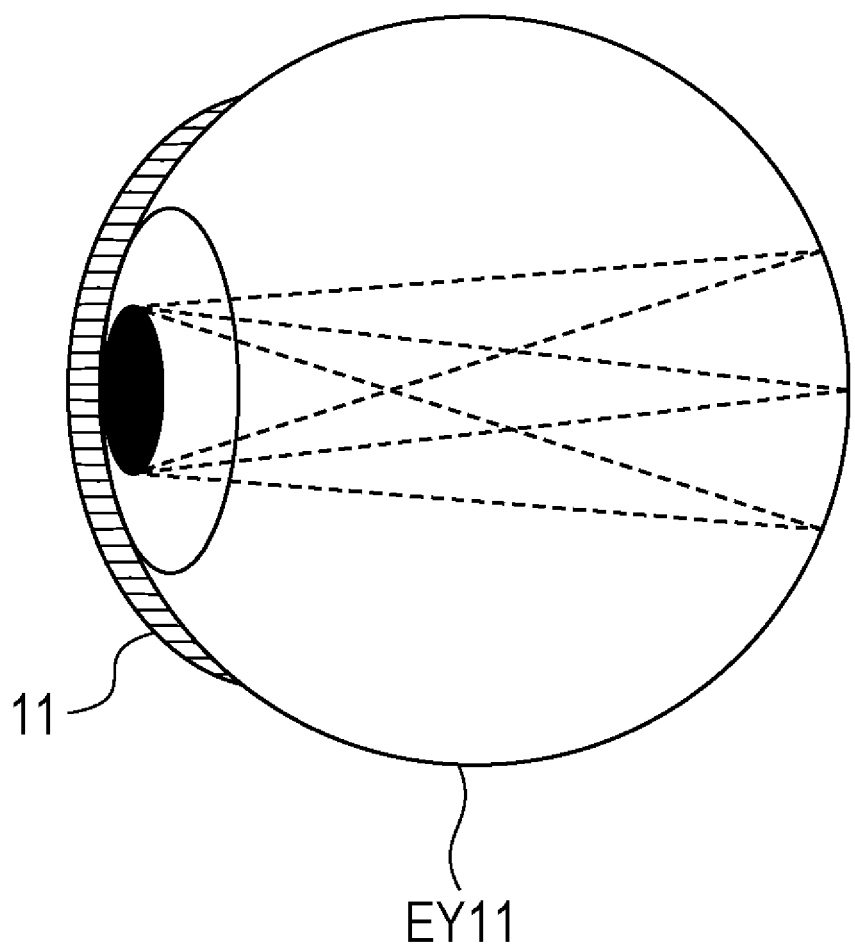
FIG. 1 is a diagram illustrating a configuration example of an external appearance of a display device.

Hereinafter, description will be given of embodiments to which the present technology is applied, with reference to the drawings.

First Embodiment

<Configuration Example of Contact Lens Type Display Device>

The present technology relates to a contact lens type display device.

Since the contact lens type display device is mounted to the eyeball of the user and used wirelessly, when using the function of the display device, the user is capable of operations such as walking around freely with the display device still mounted. However, using external equipment such as a camera or a detection device to perform a selection motion operation of a cursor, a pointer, or the like in relation to information in a displayed screen, determination of the opening and closing of the eyelid of the user, determination of whether or not the user is awake, or the like results in burdening or restricting the user.

Therefore, in the present technology, by providing a light receiving element in the proximity of display elements which display an image, a user interface for performing operations of a cursor, a pointer, or the like without an external device other than the display device being necessary can be realized.

In the contact lens type display device, light that is emitted by the display elements and reflected on the surface of the eyeball is detected by a light receiving element. In this case, the reflected light is detected at the white or the iris of the surface of the eyeball. Conversely, in the pupil, since the light is transmitted into the eyeball, there is little reflected light. Therefore, a portion at which the reflected light is weak is detected as the pupil, and a line of sight is detected from the motion of the detected pupil.

Therefore, since it becomes possible to specify the direction in which the eyeball is facing, it becomes possible to provide a user interface for performing operations of a cursor, a pointer, or the like without using an external device, and it is possible to improve the usability of the display device with a simple configuration.

In the present technology, by providing a light receiving element, a pressure sensor, a temperature sensor, and the like inside the display device, it is possible to determine (detect) the opening and closing of the eyelid of the user based on the output of these elements and sensors.

For example, it is possible to determine the opening and closing of the eyelid without requiring an external device other than the display device by detecting whether light from the outside is received by the light receiving element, or by detecting whether light that is emitted from the display device toward the outside is reflected on the underside of the eyelid of the user. Furthermore, for example, it is also possible to detect the opening and closing of the eyelid without using an external device other than the display device by detecting the pressure applied to the display device by the eyelid or the like of the user.

In the present technology, it is possible to detect the opening and closing of the eyelid of the user at high precision using a simpler configuration, without providing an external device other than the display device. As a result, it is possible to improve the usability of the display device.

Next, description will be given of specific embodiments of a contact lens type display device to which the present technology is applied.

The contact lens type display device is mounted on an eyeball of a user as illustrated in FIG. 1.

In FIG. 1, a contact lens type display device 11 is mounted to a surface of an eyeball EY11 of a user. The contact lens type display device 11 is formed in a shape capable of being mounted to and removed from the eyeball EY11 of the user, as with a so-called contact lens.

Figure 2:
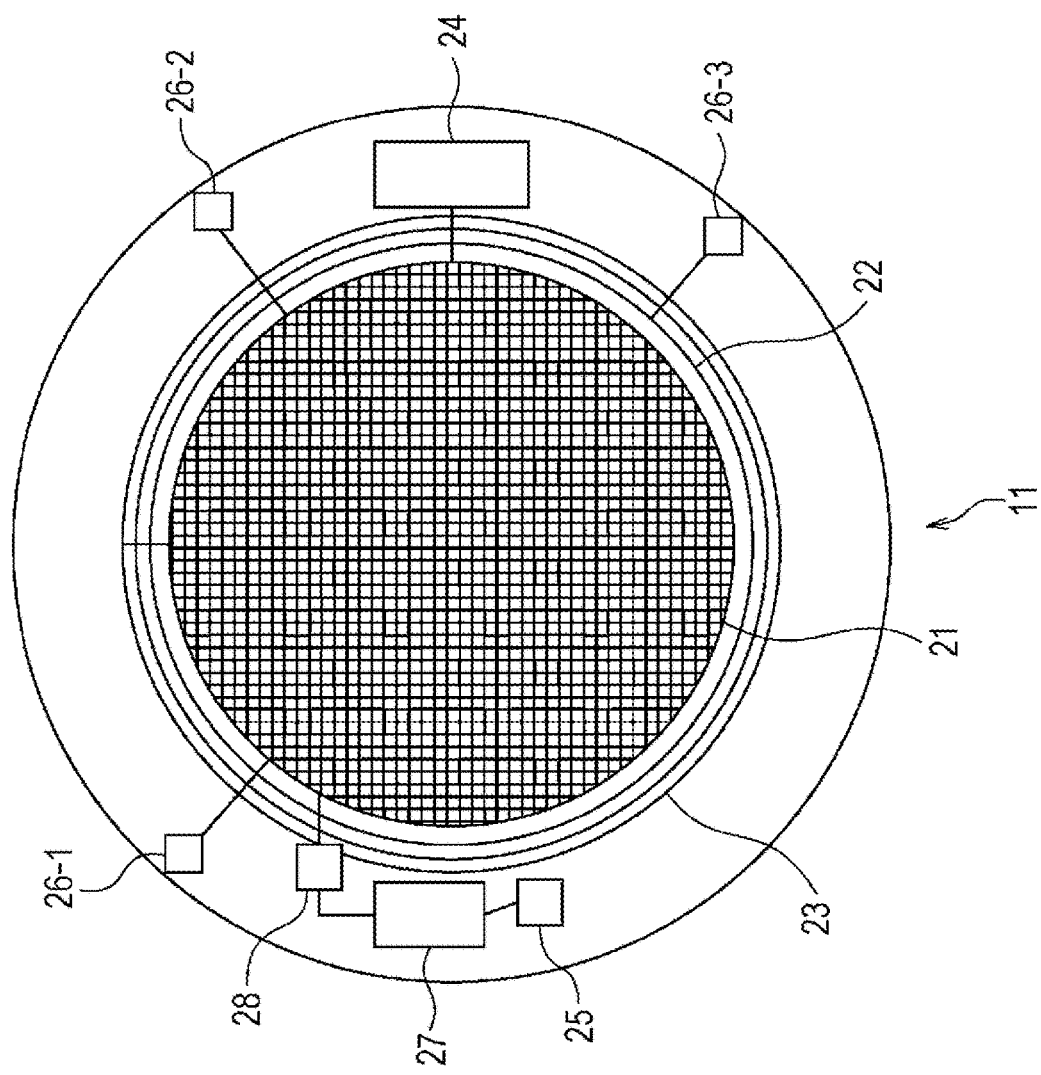
FIG. 2 is a diagram illustrating a configuration example of the display device.

Such a display device 11 is configured as illustrated in FIG. 2, for example.

In other words, the display device 11 includes a display region 21, an electrical supply antenna 22, a signal antenna 23, an electrical generation unit 24, a posture detection unit 25, a tear detection unit 26-1, a tear detection unit 26-2, a tear detection unit 26-3, a signal processing unit 27, and a display element drive unit 28.

Note that, FIG. 2 is a diagram of the display device 11 as seen from the left toward the right in FIG. 1, that is, is a diagram of the user to which the display device 11 is mounted as seen from the front, and the display device 11 is a circular shape in FIG. 2.

The display region 21 includes a display element formed of a plurality of display pixels which display information such as an image or characters to be presented to the user, and a light receiving element for line of sight detection, which is disposed adjacent to the display element and receives the light that is reflected on the surface of the eyeball of the user. Furthermore, the display region 21 includes a light emitting element and a light receiving element for detecting the opening and closing of the eyelid of the user.

The electrical supply antenna 22 is provided so as to surround the display region 21, and receives induced electrical power caused by a magnetic field or an electrical field supplied from outside. The signal antenna 23 transmits information that is supplied from the signal processing unit 27 such as the result of performing a user interface operation based on the line of sight of the user to the outside, receives the information that is transmitted thereto from the outside such as information to be displayed on the display pixels, and supplies the received information to the signal processing unit 27.

The electrical generation unit 24 obtains and accumulates power by rectifying an induced current that is generated by the electrical supply antenna 22 due to electromagnetic induction caused by an electrical field from outside, and supplies the power to each part of the display device 11. Note that, when the electrical generation unit 24 performs electrical generation itself using a predetermined method, or when the electrical generation unit 24 includes a rechargeable battery, the display device 11 may not be provided with the electrical supply antenna 22.

The posture detection unit 25 is formed of an electronic gyroscope, an accelerometer, and the like, detects the posture and the movement of the user to which the display device 11 is mounted, and supplies the detection result to the signal processing unit 27. For example, the movement of the head of the user and the posture of the user are detected by the posture detection unit 25.

The tear detection unit 26-1 to the tear detection unit 26-3 sample tears which are excreted from the user, and performs measurement of a tear excretion amount and component analysis of the tears that are obtained. Note that, hereinafter, when it is not particularly necessary to distinguish the tear detection unit 26-1 to the tear detection unit 26-3, they will be referred to simply as the tear detection unit 26.

The signal processing unit 27 controls the entire display device 11. For example, the signal processing unit 27 detects the line of sight of the user by detecting the difference (the difference) in the amount of light received by the light receiving element disposed in each region of the display device 11 based on the signals that are supplied from the light receiving element for line of sight detection of the display region 21. For example, the signal processing unit 27 detects the opening and closing of the eyelid of the user based on the signal which is supplied from the light receiving element for eyelid open-close detection of the display region 21.

The signal processing unit 27 controls the display element drive unit 28 based on the detection result that is supplied from the posture detection unit 25, the detection result of the line of sight, the information that is received by the signal antenna 23, and the like, and causes the display region 21 to display an image or the like.

Specifically, for example, when the display device 11 is rotated in relation to the eyeball of the user, it is possible to detect the rotation direction and the rotation amount in the posture detection unit 25. Therefore, the signal processing unit 27 controls the display element drive unit 28 and causes the image that is being displayed on the display region 21 to rotate by the rotation amount of the display device 11 in the opposite direction from the rotation direction of the display device 11, which is supplied from the posture detection unit 25, in relation to the eyeball. Accordingly, even if the display device 11 rotates on the eyeball of the user, the rotation of the image which occurs as a result is corrected, and it is possible to provide the image to the user in an easily viewable manner.

The display element drive unit 28 drives the display element of the display region 21 according to the control of the signal processing unit 27 and causes the image to be displayed, and causes the light emitting element of the display element drive unit 21 to emit light according to the control of the signal processing unit 27.

Note that, hereinafter, the signal that is output from the light receiving element of the display region 21 and corresponds to the amount of light received by the light receiving element will be referred to as the received light signal.

Figure 3:
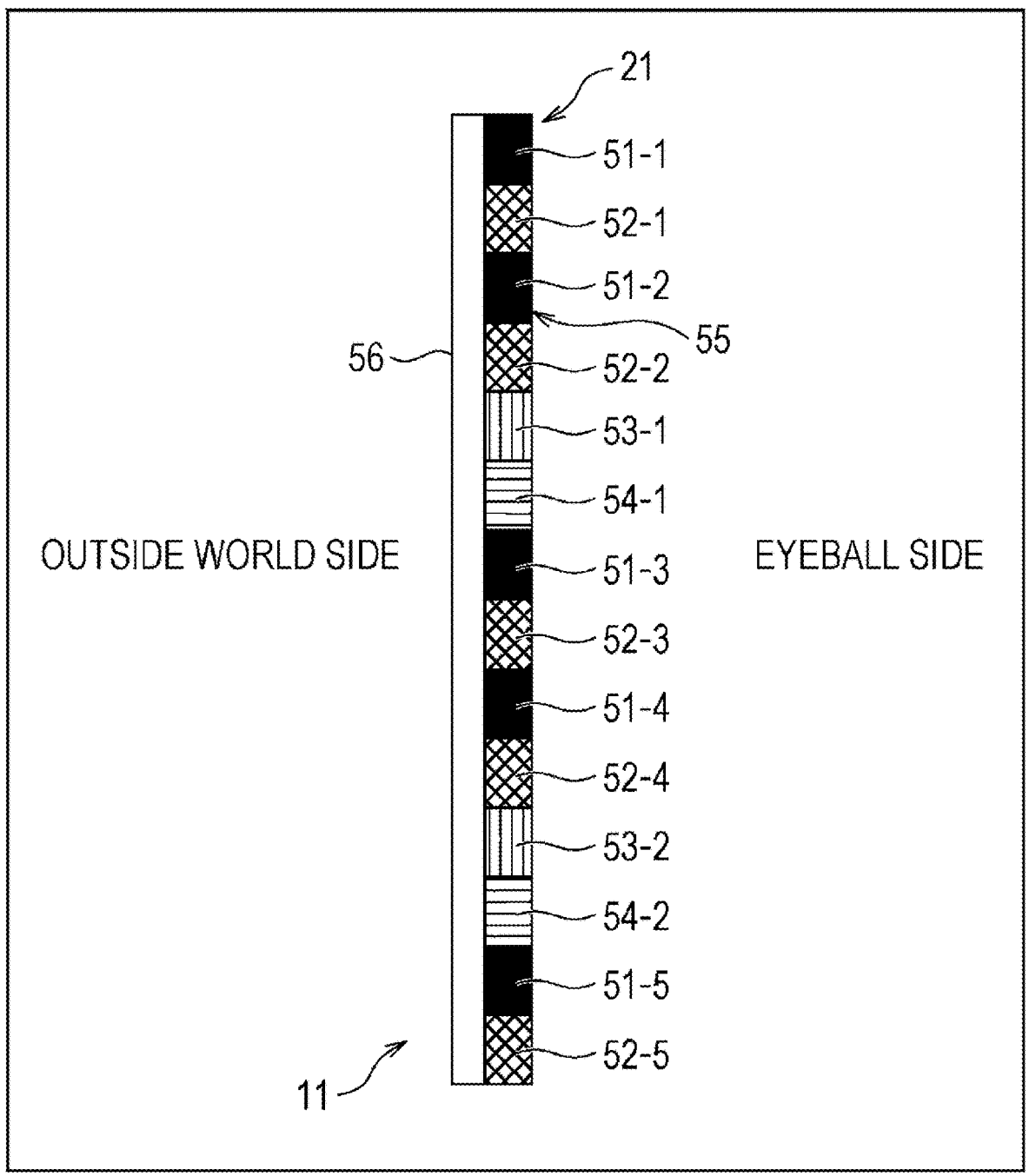
FIG. 3 is a diagram illustrating a configuration example of a display region.

The display region 21 of the display device 11 is configured as illustrated in FIG. 3, for example. Note that, FIG. 3 illustrates a portion of a cross section of the display device 11, when the display device 11 is viewed from the depth direction in FIG. 1.

In FIG. 3, display pixel 51-1 to display pixel 51-5 which display information such as an image, and light receiving element 52-1 to light receiving element 52-5 for line of sight detection, which receive the light that is reflected from the surface of the eyeball of the user are provided in the display region 21 of the display device 11.

Light emitting element 53-1 and light emitting element 53-2 for eyelid open-close detection, and light receiving element 54-1 and light receiving element 54-2 for eyelid open-close detection are provided in the display region 21. The light emitting elements 53-1 and 53-2 emit light toward the outside, and the light receiving elements 54-1 and 54-2 receive light that is incident thereto from the outside.

A single display device formed of the display pixel 51-1 to the display pixel 51-5 is a display element 55.

Note that, hereinafter, when it is not particularly necessary to distinguish the display pixel 51-1 to the display pixel 51-5, they will be referred to simply as the display pixel 51. Hereinafter, when it is not particularly necessary to distinguish the light receiving element 52-1 to the light receiving element 52-5, they will be referred to simply as the light receiving element 52.

Furthermore, hereinafter, when it is not particularly necessary to distinguish the light emitting element 53-1 and the light emitting element 53-2, they will be referred to simply as the light emitting element 53, and when it is not particularly necessary to distinguish the light receiving element 54-1 and the light receiving element 54-2, they will be referred to simply as the light receiving element 54.

The display element 55 is configured of a liquid crystal display element, an organic electroluminescence (OLED (Organic Light Emitting Diode)) display element, or the like. In the example of FIG. 3, the display pixels 51 and the light receiving elements 52 are lined up alternately in the vertical direction on the right side in the drawing of the display device 11, that is, the side of the eyeball of the user, and the light emitting elements 53 and the light receiving elements 54 are disposed partially between the elements.

Therefore, for example, in FIG. 2, the display pixels 51 and the light receiving elements 52 are disposed to be lined up alternately in the vertical direction and the horizontal direction in the display region 21, and the light emitting element 53 and the light receiving element 54 are disposed in portions of the region.

A lubrication layer 56 is provided on the left side in the drawing of the display pixels 51 and the light receiving elements 52 in the display device 11, that is, on the outside of the display device 11. The lubrication layer 56 is formed of a transparent synthetic resin or the like, for example, and when the user mounts the display device 11 to the eye, the eyelid of the user is capable of moving smoothly due to the lubrication layer 56.

Note that, in FIG. 3, description is given of an example in which the display pixels 51 and the light receiving elements 52 are in close contact with the light emitting elements 53 and the light receiving elements 54; however, it is not necessary for the elements to be in close contact, and gaps may be provided between the display pixels 51 and the light receiving elements 52 or the like. In FIG. 3, one light receiving element 52 is provided for one display pixel 51; however, one light receiving element 52 may be provided for a plurality of display pixels 51.

Here, description will be given of the detection of the line of sight of the user, and the detection of the opening and closing of the eyelid of the user.

First, description will be given of the detection of the line of sight of the user.

For example, light is output from the display pixels 51 toward the right side in FIG. 3, that is, the eyeball side. Of the light that is output from the display pixels 51, the light that is incident on the opaque portion such as the white and the iris of the eyeball EY11 illustrated in FIG. 1 is absorbed and reflected by the surface of the eyeball EY11.

Therefore, in regions opposing the white, the iris, and the like in the display region 21, a portion of the light that is output from the display pixels 51 is reflected by the surface of the eyeball EY11 and received (detected) by the light receiving elements 52.

Conversely, since the pupil portion in the eyeball EY11 is transparent, of the light that is output from the display pixels 51, the light that is incident on the pupil is not substantially reflected by the pupil, reaches the retina in the eyeball EY11, and is absorbed by the retina. Therefore, in regions opposing the pupil in the display region 21, the light that is output from the display pixels 51 is not substantially detected by the receiving elements 52.

In this manner, by detecting the difference (difference) in the amount of light from the display pixels 51 that is detected by each of the light receiving elements 52, it is possible to determine the direction of the eyeball EY11 which indicates the direction in which the eyeball EY11 (the pupil) is facing, that is, to determine the direction of the line of sight of the user. In particular, if the direction of the line of sight of the user can be determined at each time, the movement of the eyeball, that is, the movement of the line of sight can be detected, and it is possible to estimate the mental state and emotions of the user from the movement of the line of sight.

Next, description will be given of the opening and closing of the eyelid of the user.

The light emitting elements 53 output light toward the left side in FIG. 3, that is, toward the outside.

At this time, for example, if the user is in a state of closing the eyelid, the light that is output from the light emitting elements 53 is reflected by the underside of the eyelid of the user, is incident on the light receiving elements 54 that are positioned in the proximity of the light emitting elements 53, and is received by the light receiving elements 54.

Meanwhile, when light is output from the light emitting elements 53, if the user is in a state of opening the eyelid, the light that is output from the light emitting elements 53 proceeds as it is to the outside. Therefore, the light that is output from the light emitting elements 53 in this state is not incident on the light receiving elements 54. In other words, in the light receiving elements 54, the light from the light emitting elements 53 is not detected.

In this manner, by detecting the change (the difference) in the amount of light from the light emitting elements 53 that is received by the light receiving elements 54 at each time, it is possible to determine (detect) whether eyelid of the user is open or closed. It is possible to use the determination result of the opening and closing of the eyelid that is obtained in this manner in the determination of whether the user is in a conscious state or a sleeping state, and in the drive control of the display device 11.

When detecting the opening and closing of the eyelid of the user, if the light emitting elements 53 are caused to emit light in a specific light emission pattern, that is, if signals of specific waveforms are superposed, it is possible to easily separate the light from the outside and the light from the light emitting elements 53.

Note that, the disposition of the light receiving element 54 that detects the light that is output from the light emitting element 53 and reflected by the underside of the eyelid of the user, may be a position approximately several pixels from the light emitting elements 53, that is, a position approaching a distance worth approximately several display pixels 51. The light receiving element 54 may be provided to be adjacent to the light emitting element 53; however, when the distance between the light emitting element 53 and the light receiving element 54 is excessively close, there is a case in which the light that is output from the light emitting element 53 is incident on the light receiving element 54. Therefore, it is preferable for the light receiving element 54 to be disposed in a position that is distanced one or more pixels from the light emitting element 53.

Here, the light emitting elements 53 and the light receiving elements 54 for eyelid open-close detection are provided separately from the display pixels 51 and the light receiving elements 52 that are used in the line of sight detection; however, a portion of the display pixels 51 and the light receiving elements 52 may be used for eyelid open-close detection. In such a case, the display pixels 51 which are also used for eyelid open-close detection are configured to emit light toward both the outside and the eyeball side. The light receiving elements 52 which are also used for eyelid open-close detection are configured to receive the light that is incident from the outside in addition to the light that is incident from the eyeball side.

As the elements for eyelid open-close detection, only the light receiving elements 54 may be provided, without providing the light emitting elements 53. In such a case, the open-close determination of the eyelid is performed based on a received light signal that is obtained by the light receiving elements 54 receiving light from the outside.

In other words, when the eyelid of the user is open, much light is incident on the light receiving elements 54 from the outside; however, when the eyelid of the user is closed, light is not substantially incident on the light receiving elements 54 from the outside. Therefore, even if the light emitting elements 53 are not particularly provided, it is possible to determine the opening and closing of the eyelid of the user based on the received light signals that are output from the light receiving elements 54.

Note that, the open-close determination of the eyelid of the user may be performed based on only the received light signals that are output from the light receiving elements 54, and may be performed based on the output of other sensors or the like.

In FIG. 3, description is given of an example in which the display pixels 51 and the light receiving elements 52 are provided in the display region 21 in close contact with each other; however, transmission regions which transmit environmental light from the outside may be provided in the display region 21.

Figure 4:
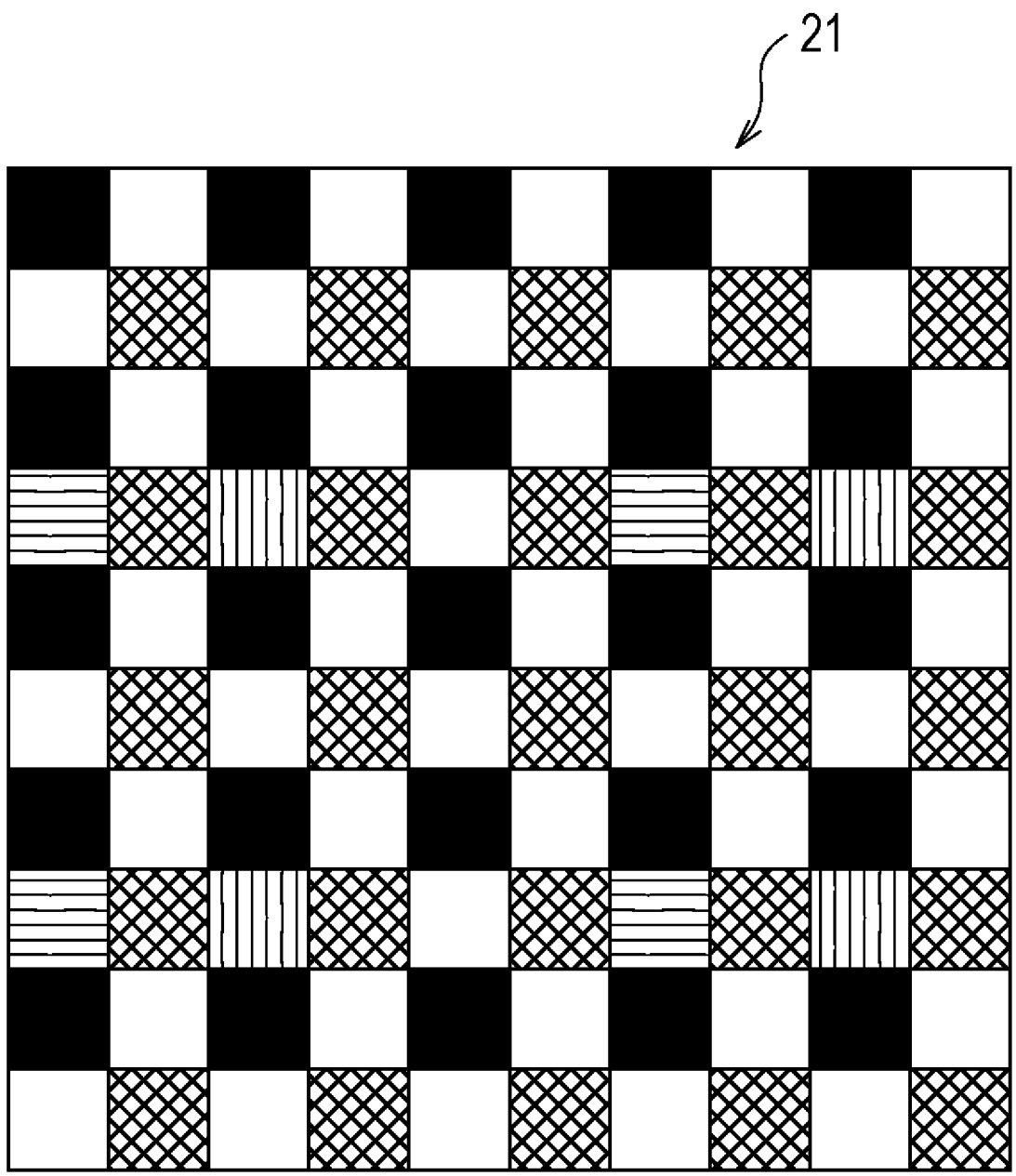
FIG. 4 is a diagram illustrating another configuration example of the display region.

In such a case, the display region 21 is configured as illustrated in FIG. 4, for example. Note that, the vertical direction and the horizontal direction in FIG. 4 correspond to the vertical direction and the horizontal direction in FIG. 2, for example. In FIG. 4, one square region represents a display pixel 51, a light receiving element 52, a light emitting element 53, a light receiving element 54, or a transmission region.

Specifically, a black square represents the region of one display pixel 51, and a square that is hatched with oblique lines represents the region of one light receiving element 52. A square that is hatched with vertical lines represents one light emitting element 53, a square that is hatched with horizontal lines represents one light receiving element 54, and a white square represents a transmission region.

Here, the transmission region is a region with a light transmittance (transparency) greater than the display pixel 51, the light receiving element 52, the light emitting element 53, and the light receiving element 54.

In this example, pairs of the light emitting elements 53 and the light receiving elements 54 are disposed discretely in the display region 21, and comparatively many transmission regions are provided overall.

By providing the transmission regions which transmit the light (environmental light) from the outside in the periphery of each of the display pixels 51, the user can view the surroundings even when the display device 11 is mounted.

Figure 5:
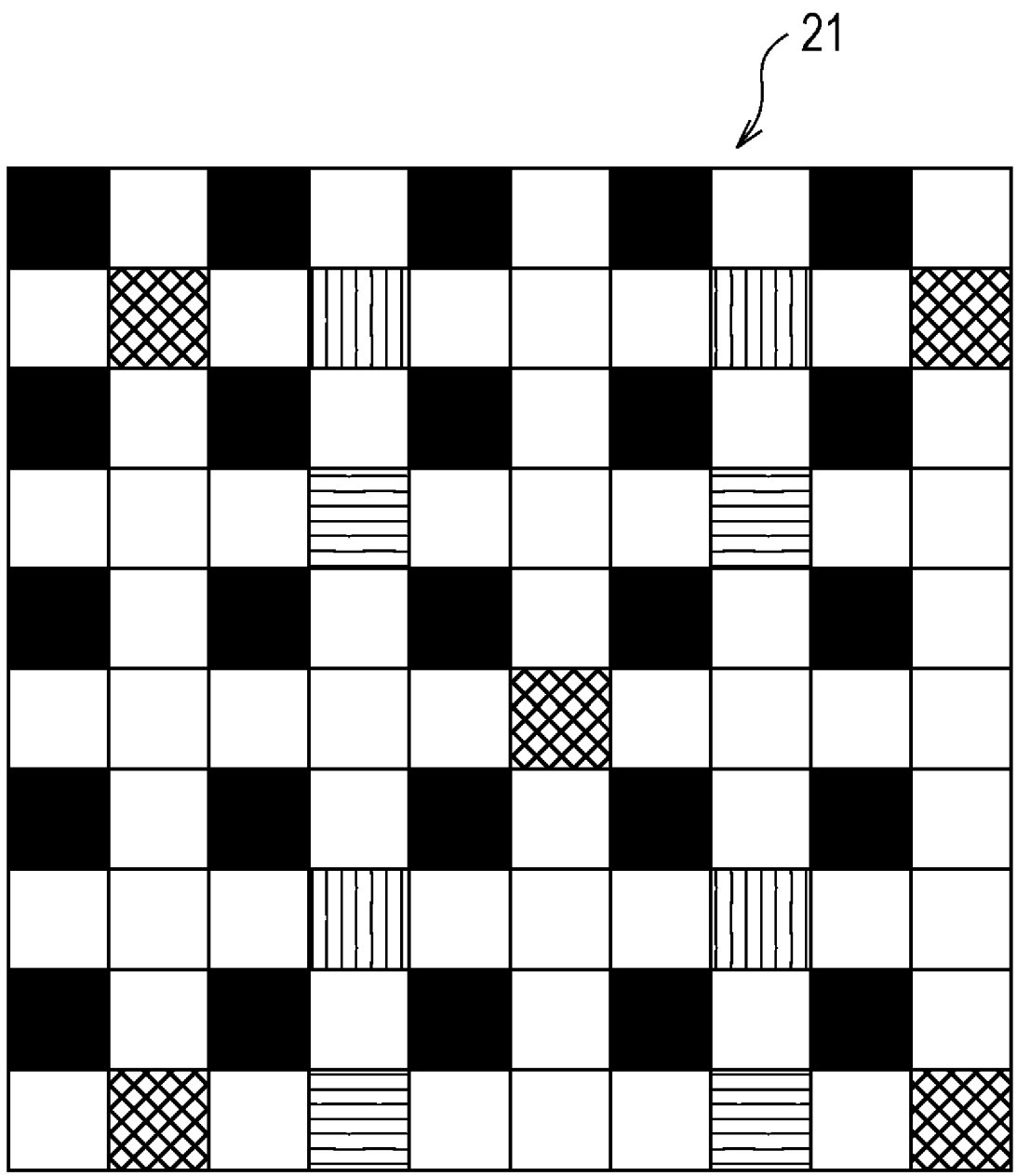
FIG. 5 is a diagram illustrating another configuration example of the display region.

The configuration is not limited to the example illustrated in FIG. 4, and, for example, the display pixels 51, the light receiving elements 52, and the like may be disposed as illustrated in FIG. 5.

Even in FIG. 5, a black square represents the region of one display pixel 51, and a square that is hatched with oblique lines represents the region of one light receiving element 52. A square that is hatched with vertical lines represents one light emitting element 53, a square that is hatched with horizontal lines represents one light receiving element 54, and a white square represents a transmission region.

In the example of FIG. 5, the number of the light receiving elements 52 that are provided in the display region 21 is less than the number of the display pixels 51 that are provided in the display region 21, and more of the transmission regions are provided corresponding to this amount. Therefore, in this example, it is possible to increase the amount of light (environmental light) from the outside of the display device 11 that is transmitted by the display region 21, and the user can view the surroundings in a brighter manner in comparison to the example illustrated in FIG. 4.

<Functional Configuration Example of Display Device>

Next, description will be given of a functional configuration example of the display device 11 that is described above.

Figure 6:
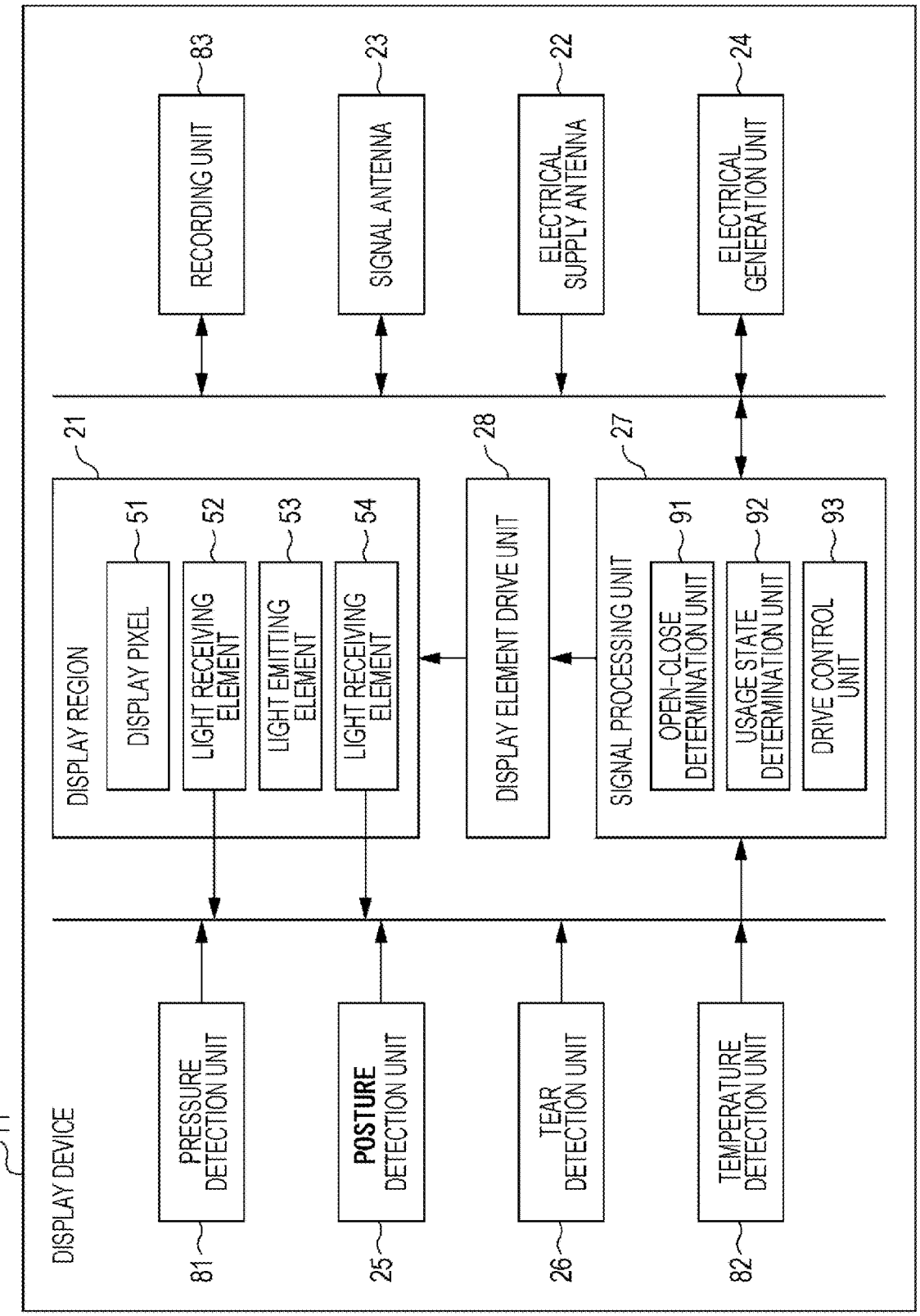
FIG. 6 is a diagram illustrating a functional configuration example of the display device.

The functional configuration of the display device 11 is configured as illustrated in FIG. 6, for example. Note that, in FIG. 6, portions corresponding to those of the cases in FIG. 2 or 3 are assigned the same reference numerals, and description thereof will be omitted as appropriate.

The display device 11 illustrated in FIG. 6 includes the display region 21, the electrical supply antenna 22, the signal antenna 23, the electrical generation unit 24, the posture detection unit 25, the tear detection unit 26, the signal processing unit 27, the display element drive unit 28, a pressure detection unit 81, a temperature detection unit 82, and a recording unit 83.

The display pixels 51, the light receiving elements 52, the light emitting elements 53, and the light receiving elements 54 are provided in the display region 21. The signal processing unit 27 includes an open-close determination unit 91, a usage state determination unit 92, and a drive control unit 93.

The pressure detection unit 81 is formed of a pressure sensor or the like, detects a pressure that is applied to the display device 11, and outputs a detection result. The output from the pressure detection unit 81 is used in the open-close determination of the eyelid or the like, for example.

The temperature detection unit 82 is formed of a plurality of temperature sensors, measures the temperature of the surface of the eyeball of the user, the temperature of the eyelid of the user, or the external temperature, and outputs a measurement result. The output of the temperature detection unit 82 is used in the determination of the body temperature of the user or the usage state of the user, the open-close determination of the eyelid, and the like.

Here, the usage state of the user refers to either a state in which the user is conscious or a state in which the user is sleeping. Therefore, in usage state determination, the state of the user is determined to be either the conscious state or the sleeping state.

The recording unit 83 is formed of non-volatile memory, for example, and records data that is supplied from the signal processing unit 27, supplies the recorded data to the signal processing unit 27, and the like.

In the display device 11, the outputs of the light receiving element 52, the light receiving element 54, the pressure detection unit 81 the posture detection unit 25, the tear detection unit 26, and the temperature detection unit 82 are supplied to the signal processing unit 27. In the display device 11, the recording unit 83, the signal antenna 23, the electrical supply antenna 22, and the electrical generation unit 24 are also connected to the signal processing unit 27.

The open-close determination unit 91 of the signal processing unit 27 performs the open-close determination of the eyelid of the user using at least one of the output of the light receiving element 54, the output of the pressure detection unit 81, or the output of the temperature detection unit 82. The usage state determination unit 92 determines the usage state of the user using the output of at least one of the light receiving element 52, the light receiving element 54, the pressure detection unit 81, the posture detection unit 25, the tear detection unit 26, or the temperature detection unit 82.

The drive control unit 93 controls the driving of each part of the display device 11, such as the display element drive unit 28, the signal antenna 23, and the electrical generation unit 24.

<Light Receiving Element for Line of Sight Detection>

Next, more detailed description will be given of each part of the display device 11.

First, description will be given of the light receiving element 52 for line of sight detection.

The received light signal that is output from the light receiving element 52 can be used in the detection of living body information of the user, more specifically, detection of pulse information, in addition to the detection of the line of sight direction of the user described above.

For example, in the display device 11, the display pixel 51 outputs light of a predetermined wavelength, and the light receiving element 52 receives the reflected light which is generated by the reflection of the light on the surface of the eyeball. The signal processing unit 27 detects the pulse of the heartbeat of the user to which the display device 11 is mounted, based on the value of the received light signal that is supplied from the light receiving element 52.

Figure 7:
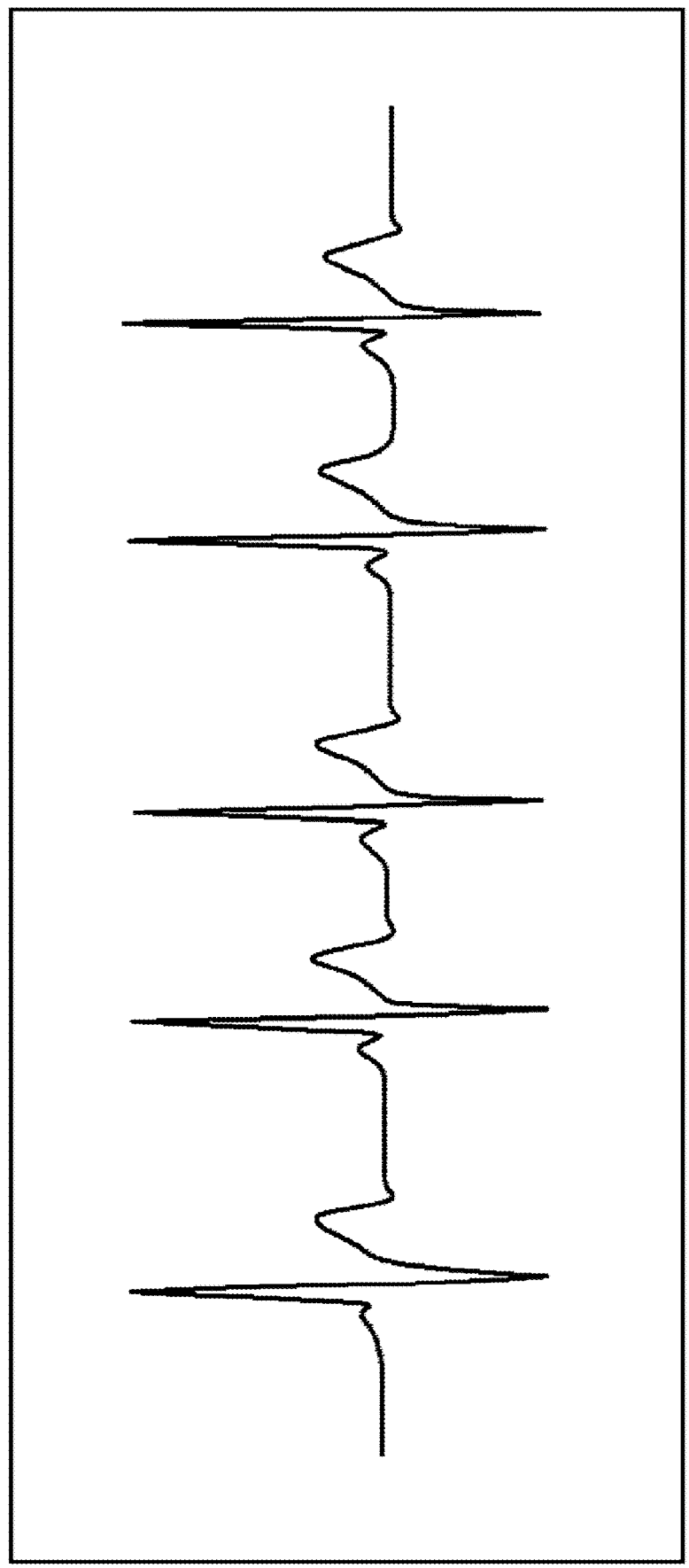
FIG. 7 is a diagram illustrating a pulse of a heartbeat.

For example, the pulse of the heartbeat occurs periodically as illustrated in FIG. 7, the time of a pulse is short in relation to the period, and blood flow is generated at the timing of the pulse. Note that, in FIG. 7, the horizontal axis illustrates time, and the vertical axis illustrates the value of the received light signal, that is, the amount of blood flow.

In FIG. 7, the portions at which the blood flow amount changes sharply are pulse portions, and it can be understood that the pulse occurs periodically.

Since the amount of blood flowing in capillary vessels increases at the timing at which the blood flow is great in a pulse, it becomes possible to detect the pulse from the presence or absence of the blood flow. There are capillary vessels in the eyeball, and there is a blood flow that matches the pulse of a heartbeat.

The light absorption spectral characteristics differ between oxyhemoglobin and deoxyhemoglobin, which are components in the blood, on the side of shorter wavelengths than 805 nm, the absorption coefficient of deoxyhemoglobin is higher, and on the side of longer wavelengths than 805 nm, the absorption coefficient of oxyhemoglobin is higher.

Therefore, the signal processing unit 27 controls the display element drive unit 28, causing light of a predetermined wavelength of a wavelength shorter than 805 nm, and light of a predetermined wavelength of a wavelength longer than 805 nm to be output from the display pixel 51 in order (alternately). The signal processing unit 27 causes the light receiving element 52 to receive the light that is output from the display pixel 51 and reflected by the surface of the eyeball. Here, the light of a shorter wavelength than 805 nm may be visible light.

Note that, the light of a predetermined wavelength of a wavelength shorter than 805 nm, and the light of a predetermined wavelength of a wavelength longer than 805 nm may be caused to be output from alternately differing proximal display pixels 51 at the same time. In such a case, the signal processing unit 27 causes the light receiving elements 52 adjacent to the display pixels 51 to receive the light that is output from the display pixels 51 and reflected by the surface of the eyeball. At this time, for example, it is necessary to determine the disposition of the display pixels 51 that output the light of alternately differing wavelengths of light, or the disposition of the light receiving elements 52, as appropriate, such that the light receiving element 52 which receive the light of a predetermined wavelength output from the display pixel 51 does not receive the light of another wavelength differing from the predetermined wavelength output from the display pixel 51.

The signal processing unit 27 determines which component of the oxyhemoglobin and the deoxyhemoglobin is more greatly contained in the blood by obtaining the difference between a value of the received light signal that is obtained when the light of the short wavelength is output, and a value of the received light signal that is obtained when the light of the long wavelength is output. Furthermore, the signal processing unit 27 detects the blood flow (the change in the amount of blood flow) based on the specified result that is obtained from the difference between the received light signals, and the change in the value of the received light signals of each time in a predetermined period, that is, based on the fluctuation with time of the intensity of the reflected light that is received by the light receiving elements 52, and obtains the pulse from the detection result of the blood flow.

The hemoglobin in the blood has a strong absorption spectrum to light in a predetermined waveband, and the light that is reflected by the blood (the blood vessels) when the blood is irradiated with light of the predetermined waveband changes according to the amount of hemoglobin, which changes according to the capacity fluctuation of the blood vessels. Therefore, it is possible to detect the amount of blood flow from the intensity of the reflected light of the light with which the surface of the eyeball (the capillary vessels) is irradiated.

The signal processing unit 27 supplies pulse information indicating the pulse that is obtained in this manner, and blood flow information indicating the amount of blood flow to the recording unit 83, as necessary, and causes the recording unit 83 to record the pulse information and the blood flow information.

The signal processing unit 27 counts the pulse rate of a user for the duration of one minute from the pulse information and the blood flow information, supplies the pulse rate for each time to the recording unit 83 and causes the recording unit 83 to record the pulse rate, in a one day cycle.

The usage state determination unit 92 performs the determination of the usage state of the user based on the pulse rate, the pulse information, the blood flow information and the like.

Ordinarily, a person has a higher pulse rate when in the conscious state than in the sleeping state, that is, when the person is active. Therefore, as illustrated in FIG. 8, for example, the usage state determination unit 92 performs the determination of whether the user is in the conscious state or in the sleeping state based on the pulse rate that is obtained from the received light signals supplied from the light receiving elements 52.

Figure 8:
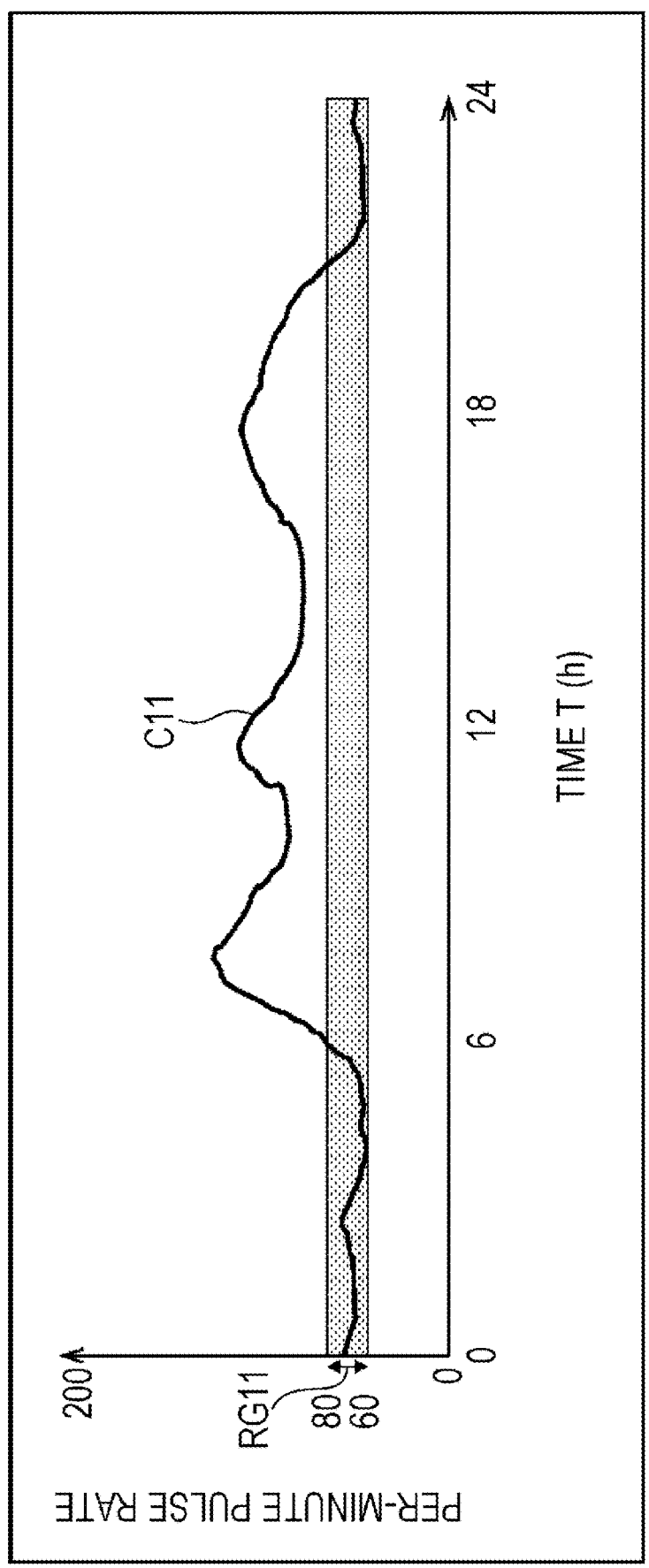
FIG. 8 is a diagram illustrating the relationship between pulse rate and a sleeping state.

In FIG. 8, the horizontal axis illustrates time (time), and the vertical axis illustrates the pulse rate at each time. In this example, a curve C11 illustrates the pulse rate at each time the pulse rate of the user is measured. In the example illustrated by the curve C11, ordinarily, it can be understood that in a period from 0:00 to 06:00, which is the time during which a person is sleeping, and approaching 24:00, the pulse rate is lower than at other times.

When the per-minute pulse rate of the present time, for example, is a value in a range between 60 and 80, that is, is a value within a range RG11 of the pulse rate in FIG. 8, the usage state determination unit 92 determines that the user is presently in the sleeping state. Meanwhile, when the pulse rate is a value outside of the range RG11, the usage state determination unit 92 determines that the user is presently in the conscious state.

Note that, the range RG11 that is used in the determination of the usage state can be determined based on the actual pulse rate of the user.

For example, when the user first mounts the display device 11 or the like, the range RG11 may be determined from the measurement results by encouraging the user to input the fact that the user will enter the sleeping state from this point, and measuring the pulse rate of the time during which the use is actually in the sleeping state. The recording unit 83 is caused to record the range RG11, for example.

Here, the input of the intent of the user to enter the sleeping state may be performed by, for example, the display device 11 displaying guidance on the display region 21, and the user performing voice input or the like using a voice recognition unit (not shown) of the display device 11 before actually sleeping, according to the guidance.

In addition to a sound characteristic recognition function, the fact that the user will enter the sleeping state may be input by the user blinking in an arbitrary pattern, the user performing an action of tilting the head or an action of shaking the head left and right, or by the user tapping the head and using the vibration.

Furthermore, the actual pulse rate of the user during sleep may be acquired for a fixed period such as approximately one week, and the range RG11 may be determined from the pulse rate that is measured during that period. A default range may be determined by managing and analyzing the data of the measured pulse rate on a cloud server, and it may be possible to use straight away even without guidance by updating the range. In addition, the data of the pulse rate for which the default range is updated every day may be corrected and recorded in the recording unit 83.

Here, it is explained that the usage state of the user is determined based on the pulse rate; however, the usage state may be determined based on the blood flow information that is obtained from the received light signals supplied from the light receiving elements 52, that is, the amount of blood flow.

<Light Receiving Element for Eyelid Open-Close Detection>

Next, description will be given of the light receiving element 54 for eyelid open-close detection.

As described above, the light receiving element 54 receives the light that is output from the light emitting element 53 and reflected by the underside of the eyelid of the user, and outputs a received light signal according to the amount of light that is received to the signal processing unit 27. Therefore, the open-close determination unit 91 can perform the open-close determination of the eyelid of the user based on the amount of received light of the received light signal that is supplied from the light receiving element 54. If the result of the open-close determination is used, it is also possible to determine the time for which the user is closing the eyelid (hereinafter, also referred to as the closed-eyelid time).

Note that, since the light from the outside is also received by the light receiving element 54 when the eyelid of the user is open, it is desirable to cause light of a specific wavelength band to be output from the light emitting element 53, and to detect the amount of received light of the wavelength band using the light receiving element 54 in order to distinguish between the light from the outside and the light from the light emitting element 53.

When the light emitting elements 53 are caused to emit light in a specific light emission pattern in order to distinguish between the light from the outside and the light from the light emitting elements 53, as described above, it is possible to discover whether or not the light from the light emitting elements 53 is detected according to whether or not the amplitude of the received light signals that are output from the light receiving elements 54 varies corresponding to the light emission pattern.

For example, if the light emitting elements 53 are caused to flash in a specific light emission pattern, it is possible to obtain the amount of light received from the light emitting elements 53 from the difference between the value of the received light signal when the light emitting elements 53 are not lit and the value of the received light signal when the light emitting elements 53 are lit. Accordingly, it is possible to perform the open-close determination of the eyelid of the user with higher precision.

When the eyelid of the user is closed, it is possible to detect the pulse information and the amount of blood flow of the user in the same manner as in the case regarding the light receiving element 52, even if the received light signals that are output from the light receiving elements 54 are used. In this case, the light that is output from the light emitting elements 53 is reflected by the underside of the eyelid of the user, and is received by the light receiving elements 54. The amount of blood flow flowing through the capillary vessels in the underside of the eyelid of the user is detected.

Therefore, the usage state determination unit 92 can determine the usage state of the user based on the blood flow information and the pulse information that is obtained according to the received light signals that are output from the light receiving elements 54.

<Pressure Detection Unit>

The pressure detection unit 81 detects a pressure that is applied to the display device 11, and outputs the detection result to the signal processing unit 27.

Therefore, for example, when the eyelid of the user is closed while the display device 11 is mounted to the user, the pressure indicated by the signal that is output from the pressure detection unit 81 becomes comparatively great. Conversely, when the eyelid of the user is open while the display device 11 is mounted to the user, the pressure that is output from the pressure detection unit 81 becomes smaller than when the eyelid is closed.

Figure 9:
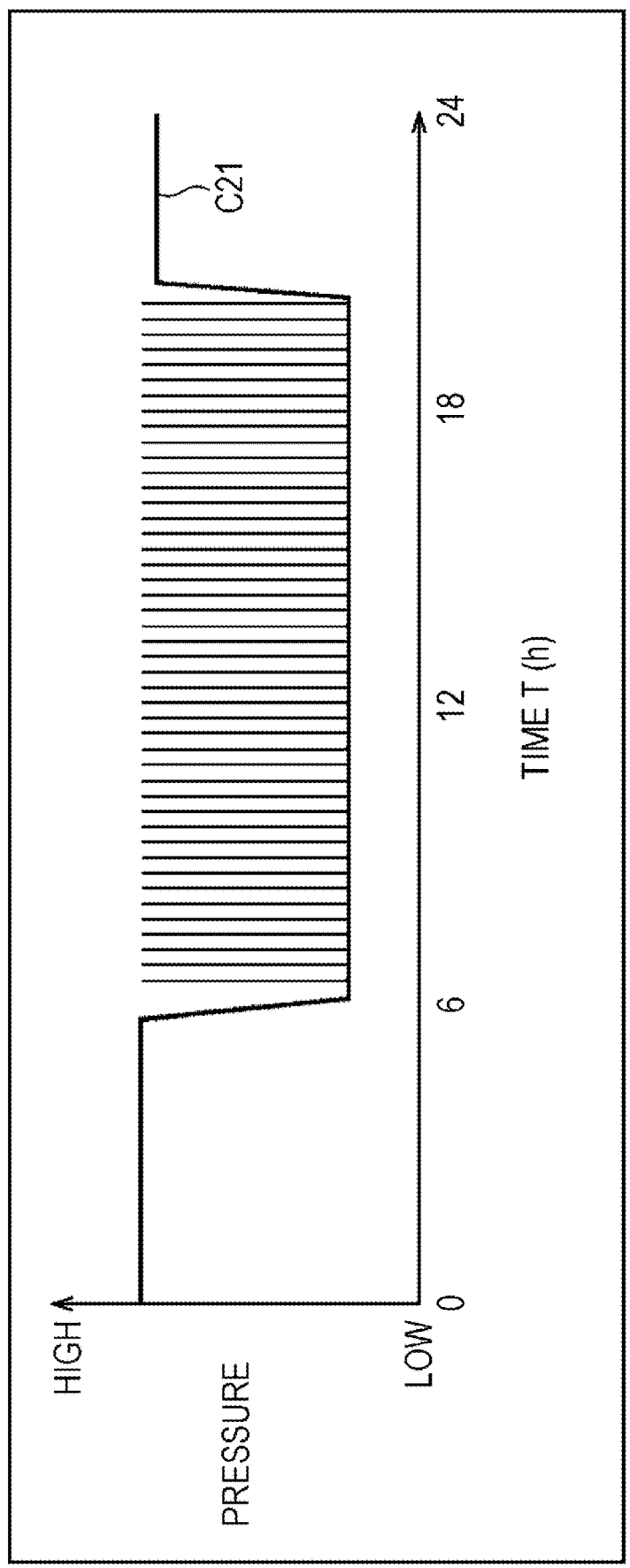
FIG. 9 is a diagram illustrating the relationship between opening and closing of an eyelid and detected pressure.

Therefore, when display device 11 is mounted to the user all day long, the measurement results illustrated in FIG. 9, for example, are obtained as the measurement results of the pressure to the display device 11 at each time.

Note that, in FIG. 9, the horizontal axis illustrates time (time), and the vertical axis illustrates the pressure to the display device 11 that is detected by the pressure detection unit 81 at each time. In this example, a polygonal curve C21 illustrates the pressure that is applied to the display device 11 that is measured at each time in relation to the user.

In the example illustrated by the polygonal curve C21, ordinarily, it can be understood that in a period from 0:00 to 06:00, which is the time during which a person is sleeping, and approaching 24:00, a pressure that is high to a certain degree is continuously applied to the display device 11. This is because the eyelid is closed when the user is sleeping, and a substantially fixed pressure is applied to the display device 11 by the eyelid.

Conversely, when the user is active, that is, in a period from 06:00 until 21:00, since the eyelid is open in a state in which the display device 11 is mounted to the user, the pressure that is detected by the pressure detection unit 81 at most times becomes lower. However, since blinking is performed even while the user is active, even in this time period, a time exists at which the pressure that is detected by the pressure detection unit 81 increases for only a short time.

The signal processing unit 27 which receives the supply of the detection (measurement) results of the pressure from the pressure detection unit 81 supplies the information indicating the supplied pressure to the recording unit 83 and causes the recording unit 83 to record the information, performs the open-close determination of the eyelid based on the information indicating the supplied pressure, and the like.

For example, the open-close determination unit 91 of the signal processing unit 27 calculates the average value of the pressure of a comparatively short time such as the average value of the pressure that is obtained by several proximal measurements based on the pressure indicated by a signal that is supplied from the pressure detection unit 81, and sets the obtained average value as the pressure to the display device 11 at the present time. When the calculated pressure is greater than or equal to a predetermined threshold, the open-close determination unit 91 determines that the eyelid of the user is closed.

Note that, in the same manner as the range RG11 of the pulse rate used in the usage state determination described above, the threshold that is used in the open-close determination of the eyelid using the pressure by the eyelid may also be calculated based on the pressure that is measured according to guidance.

Since there are blood vessels on the underside of the eyelid of the user which contact the pressure sensor that serves as the pressure detection unit 81, if the eyelid of the user is in the closed state, it is possible to obtain the pulse information of the user based on the pressure indicated by the signal that is output from the pressure detection unit 81. For example, the calculation of the pulse information when the open-close determination unit 91 determines that the eyelid is closed is performed based on the pressure that is measured by the pressure detection unit 81.

The usage state determination unit 92 performs the determination of the usage state based on the pulse information that is obtained by the pressure measurement in the pressure detection unit 81. Specifically, for example, in the same manner as the case in the example of FIG. 8, the usage state determination unit 92 determines whether the user is in the conscious state or in the sleeping state by comparing the pulse rate (the number of beats) indicated by the pulse information that is obtained in a state in which the eyelid of the user is closed, and the range that is determined in advance.

<Posture Detection Unit>

The posture detection unit 25 is configured to include single or plural electronic gyroscopes and accelerometers.

For example, when the single electronic gyroscope is used as the sensor that configures the posture detection unit 25, the inclination of the electronic gyroscope, that is, the inclination of the display device 11 is detected. Conversely, for example, when the plurality of electronic gyroscopes are used as the sensor that configures the posture detection unit 25, an inclination with a different disposition for each electronic gyroscope as a reference plane is detected. In the accelerometer that configures the posture detection unit 25, the acceleration applied to the posture detection unit 25 (the display device 11) is detected.

The information that is obtained by each sensor that serves as the posture detection unit 25 is supplied from the posture detection unit 25 to the signal processing unit 27 and is used in the posture determination which determines the posture of the user to which the display device 11 is mounted.

Note that, in order to more accurately measure the posture of the user from the output of the posture detection unit 25, it is necessary to obtain a more accurate relationship between the reference plane of each sensor that configures the posture detection unit 25 and the ground (the horizontal plane).

Therefore, when the user first mounts the display device 11 or the like, calibration of the posture information indicating the relationship between the reference plane and the ground may be performed.

In such a case, for example, the calibration may be performed when the signal processing unit 27 detects that the difference between the temperature of the eyeball side of the user and the temperature of the outside in the display device 11 supplied from the temperature detection unit 82 is greater than or equal to a predetermined value.

During the calibration of the posture information, for example, the signal processing unit 27 causes the display region 21 to display guidance (an image) urging the user to stare at a point in front of the user in a standing position posture. Therefore, the user assumes the standing position posture in accordance with the guidance, and subsequently, for example, inputs the fact that the user is in the standing position posture by voice or the like using the voice recognition unit (not shown) of the display device 11.

When the user assumes the standing position posture, the signal processing unit 27 learns the relationship between the reference plane of each sensor that configures the posture detection unit 25 and the ground based on the output of each sensor that is supplied from the posture detection unit 25, supplies information indicating the positional relationship between each reference plane and up, down, left, and right to the recording unit 83, and causes the recording unit 83 to record the information. When performing the posture determination based on the output from the posture detection unit 25, the signal processing unit 27 uses the information indicating the positional relationship of the reference planes that is recorded in the recording unit 83, as appropriate. Accordingly, it is possible to specify the posture of the user with higher precision.

Note that, during calibration, the input of the fact that the user has assumed the standing position posture that is performed by the user may be performed using any method, in addition to a method using the voice recognition function. For example, the input may be performed by the user blinking in an arbitrary pattern, the user performing an action of tilting the head or an action of shaking the head left and right, or by the user tapping the head and using the vibration.

The accuracy of the posture information and the rendering positional accuracy of the display elements 55 may be improved by using eyeball movement caused by tiny visual fixations (microsaccades). For example, assuming that the eyeball movement caused by the tiny visual fixations is movement with an angular velocity in which the center of the eyeball is a reference point, it is possible to improve the measurement accuracy of the posture information from the inclination and the acceleration of the reference plane that is obtained from each sensor that configures the posture detection unit 25 if the eyeball movement of the tiny visual fixations is detected a plurality of times and the variation in the angular velocity component of the detected eyeball movement is ignored.

It is known that the light reception characteristics of photoreceptor cells of the retina of a mammal respond more the greater the change in light. Therefore, a person can attain an image which is recognizable to the naked eye by causing the light that is input in tiny visual fixations to change randomly and causing the light to be input to constantly change and to reach the visual cortex.

When the contact lens type display device 11 is mounted to the eyeball and an image is displayed, since the contact lens type display device 11 and the eyeball move at the same time, the merit of random input by the tiny visual fixations may not be enjoyed. For example, there is a case in which different recognition is performed from an ordinary manner of seeing, such as the image being recognized in a blurred manner, according to the number of pixels of the display elements 55, the resolution of frame frequency, and the characteristics of the image being displayed.

Therefore, when the conditions for such a state are met, the entirety of the image to be displayed on the contact lens type display device 11 or a portion of the image is shifted by omega degrees and n pixels or the like, and a omega, n coefficient is set randomly, thereby, it becomes possible to correct a case in which the tiny visual fixations are reduced or the tiny visual fixations cease to be present. The pattern of the tiny visual fixations is acquired by the position of the contact lens type display device 11 and the accelerometer, subjected to pattern analysis for a fixed period, and fed back to the next prediction value in real time.

The signal processing unit 27 performs the posture determination of the user based on the signal which is supplied from each sensor of the posture detection unit 25.

Specifically, for example, when the user mounts the display device 11 and assumes the standing position posture, the electronic gyroscope that configures the posture detection unit 25 uses a plane, which is perpendicular in relation to the ground, and the normal of which is the front-rear direction as seen from the user, as a reference plane (hereinafter referred to as the vertical reference plane). A plane on the front side of the user of the vertical reference plane is assumed to be the front.

For example, when another electronic gyroscope that configures the posture detection unit 25 is perpendicular in relation to the vertical reference plane, that is, when the user mounts the display device 11 and assumes the standing position posture, the other electronic gyroscope uses a plane, which is horizontal in relation to the ground, as a reference plane (hereinafter referred to as the horizontal reference plane).

In such a case, for example, when a value close to vertical is detected by the posture detection unit 25 as the angle of the vertical reference plane in relation to the ground, the signal processing unit 27 determines that there is a high likelihood that the posture of the user is an antigravity posture such as the standing position or the sitting position.

For example, when a value close to horizontal is detected by the posture detection unit 25 as the angle of the vertical reference plane in relation to the ground, the signal processing unit 27 determines that there is a high likelihood that the posture of the user is a resting posture such as a supine position, a Sims' position, or a prone position.

In particular, when the front of the vertical reference plane is the top plane, that is, facing upward, the signal processing unit 27 determines that there is a high likelihood that the posture of the user is the supine position, and when the front of the vertical reference plane is the bottom plane (bottom facing), the signal processing unit 27 determines that there is a high likelihood that the posture of the user is the prone position.

When a value close to vertical is detected by the posture detection unit 25 as the angle of the horizontal reference plane in relation to the ground, the signal processing unit 27 determines that there is a likelihood that the posture of the user is the prone position.

The usage state determination unit 92 determines the usage state of the user based on the result of the posture determination by the signal processing unit 27.

Figure 10:
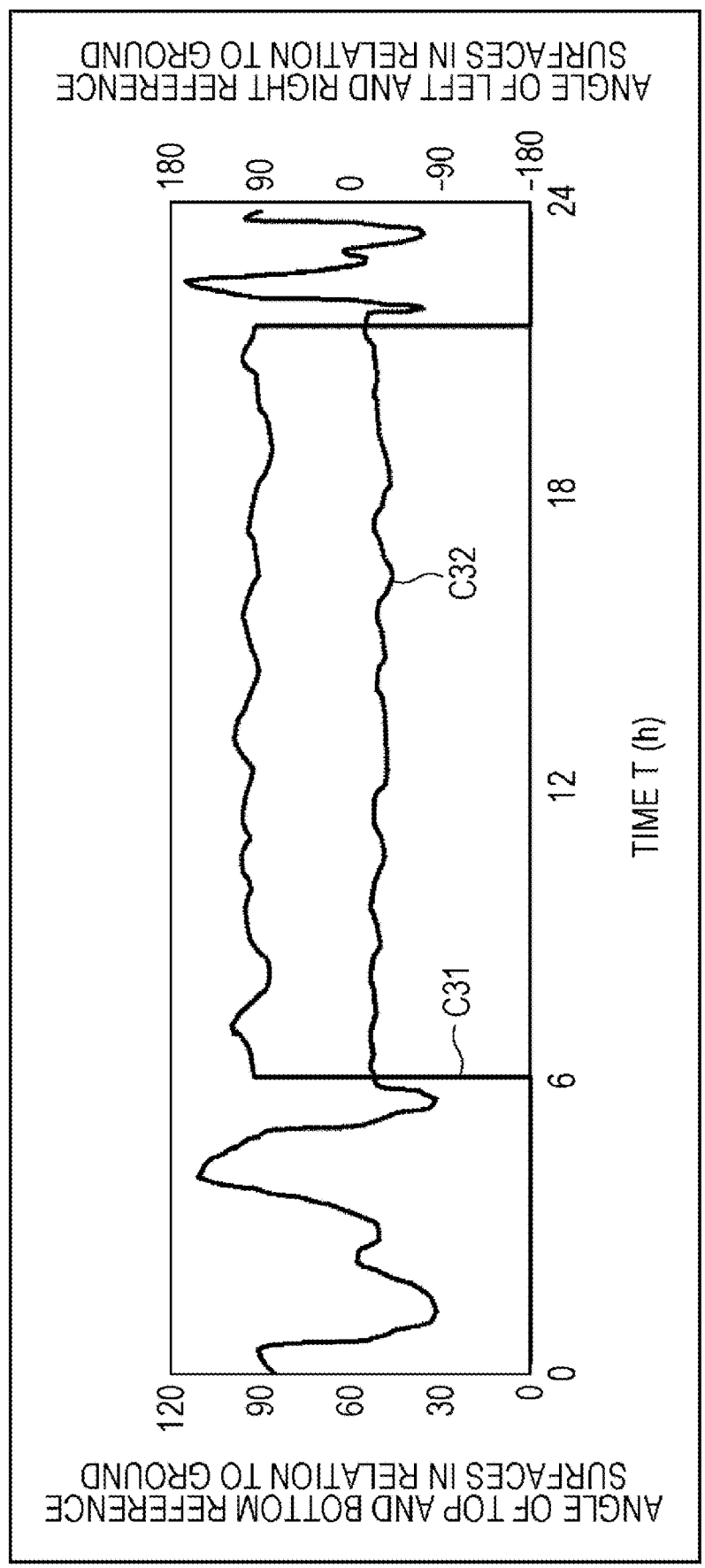
FIG. 10 is a diagram illustrating posture detection.

For example, when display device 11 is mounted to the user all day long, the measurement results illustrated in FIG. 10 are obtained as the detection results of the angle in relation to the ground of each reference plane performed by the posture detection unit 25 at each time.

Note that, in FIG. 10, the horizontal axis illustrates time (time), and the vertical axis illustrates the angle of the vertical reference plane or the horizontal reference plane in relation to the ground that is detected by the posture detection unit 25 at each time. In particular, the vertical axis of the left side in the drawing illustrates the angle between the vertical reference plane and the ground, and the vertical axis of the right side in the drawing illustrates the angle between the horizontal reference plane and the ground.

In FIG. 10, a polygonal curve C31 illustrates the angle of the vertical reference plane in relation to the ground at each time, and a polygonal curve C32 illustrates the angle of the horizontal reference plane in relation to the ground at each time.

The angle of the vertical reference plane illustrated by the polygonal curve C31, ordinarily, in a period from 0:00 to 06:00, which is the time during which a person is sleeping, and approaching 24:00, is approximately 0 degrees, and it can be understood that the user is in a lying down posture at these times. At these times, the angle of the horizontal reference plane illustrated by the polygonal curve C32 changes greatly in an irregular manner, and it can be understood that the user is turning as the user sleeps.

Conversely, since the user is often in the standing position or the sitting position posture during the time period in which the user is active, that is, a period from 06:00 until 22:00, the angle of the vertical reference plane is around 90 degrees, and the horizontal reference plane is around 0 degrees.

In the signal processing unit 27, the posture determination of the user is performed using the angle of the vertical reference plane and the angle of the horizontal reference plane at each time, or the like.

The usage state determination unit 92 performs the determination of the usage state determination unit based on the results of the posture determination performed by the signal processing unit 27. Specifically, for example, the usage state determination unit 92 determines the sleeping state when the posture is one in which the body is lain down such as the supine position, the Sims' position, or the prone position for a fixed time or longer, and, no action (movement) is detected by the posture detection unit 25 for a fixed time or longer.

Note that, the usage state determination unit 92 may determine the usage state based on the detection results of the posture and the movement performed by the posture detection unit 25 without using the results of the posture determination.

<Temperature Detection Unit>

Next, description will be given of the temperature detection unit 82.

The temperature detection unit 82 is configured to include temperature sensors, a plurality of which are disposed on the surface (the outside surface) and the underside (the eyeball side surface) of the display device 11, and temperature transmission prevention material that is provided on the joining surface between each temperature sensor and the display device 11.

In the temperature sensors, which configure the temperature detection unit 82 and are provided on the surface of the display device 11, the temperature of the outside surface of the display device 11, that is, the external temperature or the temperature of the eyelid is measured (detected). For example, in the state in which the eyelid of the user is closed, the temperature of the eyelid of the user is measured by the temperature sensors that are provided on the surface, and in the state in which the eyelid of the user is open, the external temperature is measured by the temperature sensors that are provided on the surface.

Note that, hereinafter, the temperature that is measured by the temperature sensors that are provided on the surface of the display device 11 will simply be referred to as the external temperature.

The temperature sensors which configure the temperature detection unit 82 and are provided on the underside of the display device 11 measure the temperature of the surface of the eyeball side of the user in the display device 11, that is, the temperature of the eyeball surface.

The external temperature and the temperature of the eyeball surface, which are measured by the temperature detection unit 82, are supplied to the signal processing unit 27 and used in the prediction of the body temperature of the user and the like. The measurement results of the external temperature and the temperature of the eyeball surface are supplied to the recording unit 83 from the signal processing unit 27, as appropriate, and recorded in the recording unit 83.

Note that, in order to accurately predict the body temperature of the user or the like, it is necessary to predict, in advance, information that is generate by individual differences depending on the user, for example, information of the external temperature and the rise in temperature of the eyeball surface in the state in which the eyelid of the user is closed, what degree of time the temperatures settle after, and the like.

Therefore, for example, when the user first mounts the display device 11 or the like, when a temperature difference between the surface and the underside of the display device 11, that is, a difference in the external temperature and the temperature of the eyeball surface is detected, the signal processing unit 27 causes the display region 21 to display guidance (an image) urging the user to close the eyelid. Therefore, the user closes the eyelid in accordance with the guidance, and subsequently, for example, inputs the fact that the eyelid is closed by voice or the like using the voice recognition unit (not shown) of the display device 11.

When the user is in the state in which the eyelid is closed, the signal processing unit 27 measures the rises in the external temperature and the temperature of the eyeball surface, the time taken for the temperatures to settle, and the like based on the temperatures of the surface and the underside that are output from the temperature detection unit 82, that is, the external temperature and the temperature of the eyeball surface, supplies the measurements to the recording unit 83, and causes the recording unit 83 to record the measurements.

Note that, during the measurement of the rise in temperature, the settlement time, and the like, the input by the user of the fact that the eyelid is closed may be performed using any method in addition to the method of using the voice recognition function. For example, the input may be performed by the user blinking in an arbitrary pattern, the user performing an action of tilting the head or an action of shaking the head left and right, or by the user tapping the head and using the vibration.

The measurement results of the rise in temperature, the settlement time, and the like that are obtained in this manner are used by the signal processing unit 27, as appropriate, in the prediction of the body temperature of the user and the like.

For example, when the user closes the eyelid and the rise in the temperatures of the surface and the underside of the display device 11 have settled, the signal processing unit 27 sets the temperature of the surface and the temperature of the underside, that is, the temperature of the eyelid and the temperature of the eyeball surface at that time as the reference body temperature of the user.

The signal processing unit 27 sets the temperature that is measured by the temperature sensors on the surface of the display device 11 when the user opens the eyelid to the external temperature, and predicts the body temperature of the user from the difference between the temperature that is measured by the temperature sensors on the underside of the display device 11 and the reference body temperature.

Note that, when the external temperature and the temperature of the eyelid, or the like are measured, the signal processing unit 27 uses a smoothed temperature such as the average value of temperatures over the passage of a fixed time as the temperature that is measured by the temperature sensors that are disposed on the surface of the display device 11. Accordingly, the noise element of the temperature rise or the like that occurs when the user blinks is removed, it is possible to improve the measurement accuracy of the external temperature or the like.

It is known that a phenomenon occurs when the body desires sleep in that the body temperature of the surface of the body rises. Therefore, when presenting light, video, or the like, it may be determined whether or not the presentation has the effect of encouraging sleep, using the rise in body temperature that is obtained through measurement.

When the user opens and closes the eyelid, the temperature that is measured by the temperature sensors that are provided on the surface of the display device 11 and serve as the temperature detection unit 82 changes. Therefore, the open-close determination unit 91 performs the open-close determination of the eyelid of the user based on the external temperature (the temperature of the eyelid), that is, the change in the temperature (a temperature rise) that is measure by the temperature sensors that are provided on the surface of the display device 11. For example, when the external temperature rises from a predetermined temperature that serves as a reference, it is determined that the eyelid is closed, and when the external temperature returns to the predetermined temperature that serves as the reference, it is determined that the eyelid is open.

Since the body temperature of the user and the external temperature are obtained from the output of the temperature detection unit 82, the usage state determination unit 92 determines the usage state of the used based on the temperatures.

Figure 11:
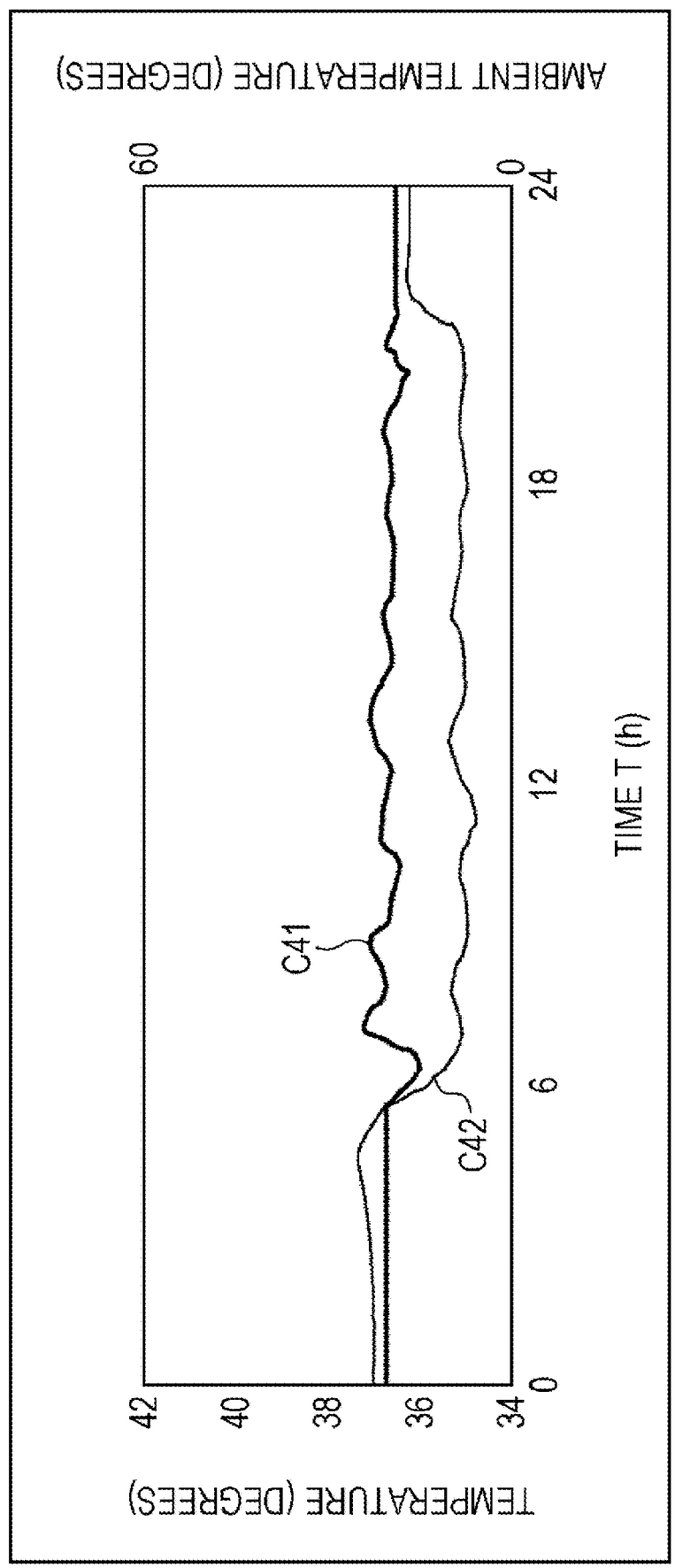
FIG. 11 is a diagram illustrating the relationship between body temperature, external temperature, and sleep.

For example, when display device 11 is mounted to the user all day long, the measurement results illustrated in FIG. 11, for example, are obtained as the measurement results of the external temperature and the body temperature of the user at each time.

Note that, in FIG. 11, the horizontal axis illustrates time (time), and the vertical axis illustrates the external temperature or the body temperature of the user at each time. In particular, the vertical axis of the left side in the drawing illustrates the body temperature, and the vertical axis of the right side in the drawing illustrates the external temperature.

In FIG. 11, a polygonal curve C41 illustrates the body temperature of the used at each time, predicted based on the output from the temperature detection unit 82. A polygonal curve C42 illustrates the external temperature at each time, measured by the temperature detection unit 82.

In this example, ordinarily, in a period from 0:00 to 06:00, which is the time during which a person is sleeping, and approaching 24:00, the body temperature and the external temperature of the user are approximately fixed temperatures. In particular, when the user is in the sleeping state, since the eyelid of the user is closed, the external temperature that is measured by the temperature detection unit 82 is the temperature of the eyelid of the user, and the temperature of the eyelid is a temperature close to the body temperature of the user.

Therefore, when the user is in the sleeping state, the difference between the external temperature and the body temperature is comparatively small, and the difference is substantially fixed.

Conversely, in a time period in which the user is active, that is, in a period from 06:00 until 21:00, since the eyelid is open in a state in which the display device 11 is mounted to the user, a state is assumed in which the difference between the body temperature of the user and the external temperature is great at most times.

Therefore, for example, when the difference between the external temperature and the body temperature is greater than or equal to a predetermined threshold, the usage state determination unit 92 determines that the user is in the conscious state.

Note that, in the same manner as the range RG11 of the pulse rate used in the usage state determination described above, for example, the threshold that is used in the usage state determination using the external temperature and the body temperature may also be calculated based on the external temperature, the reference body temperature, or the like, that is measured according to the guidance.

As is understood from FIG. 11, when the eyelid of the user is in the closed state, the external temperature, that is, the temperature of the eyelid is maintained at a substantially fixed temperature. Therefore, when the amount of change in the external temperature in a fixed time is less than or equal to a predetermined threshold, the open-close determination unit 91 may determine that the eyelid of the user is closed.

In the open-close determination unit 91, since the open-close determination of the eyelid is performed based on the body temperature of the user, the external temperature, and the like, it is possible to obtain the closed-eyelid time and the number of blinks from the opening and closing results.

The usage state determination unit 92 may perform the usage state determination based on, for example, the number of times the user blinks in a period of one minute.

Figure 12:
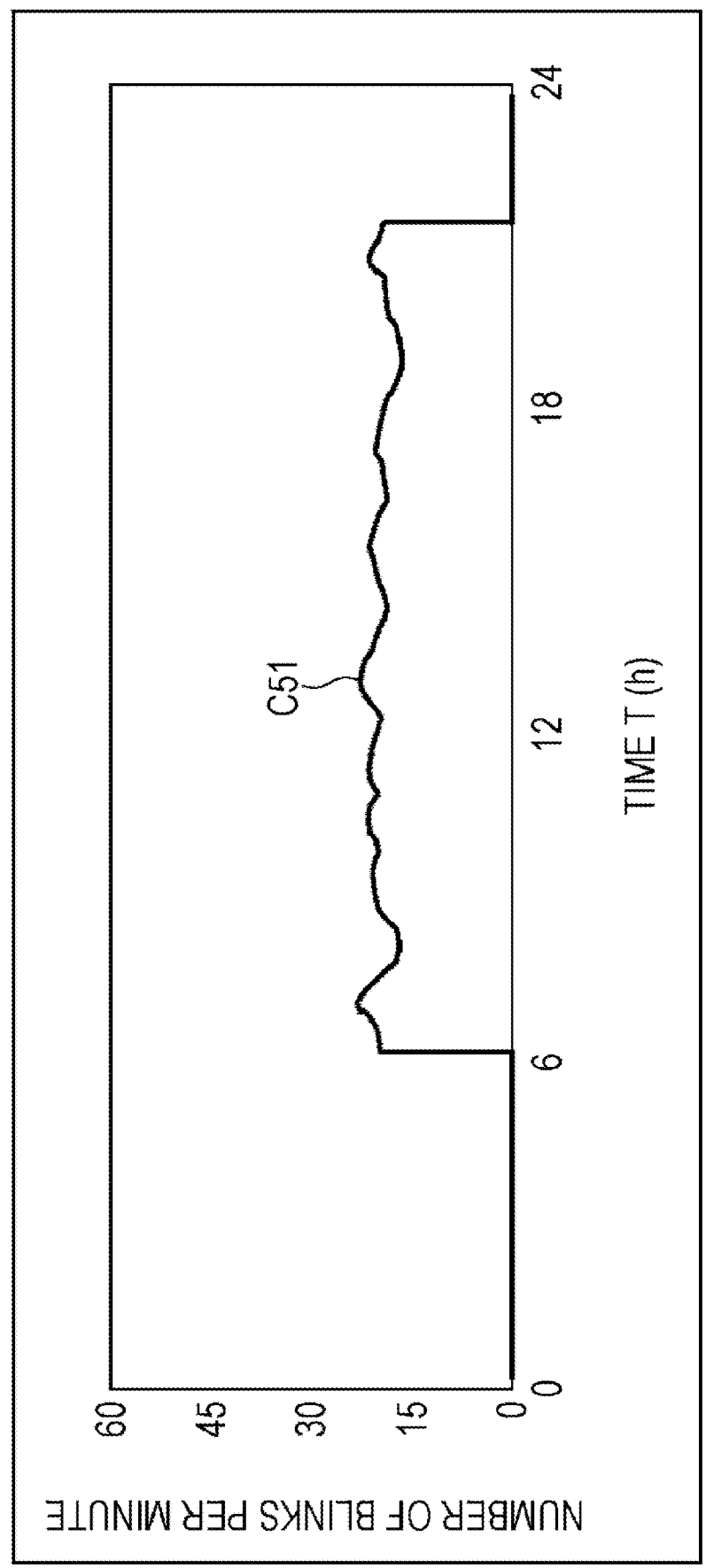
FIG. 12 is a diagram illustrating the relationship between blinking and sleep.

For example, when display device 11 is mounted to the user all day long, the measurement results illustrated in FIG. 12, for example, are obtained as the measurement results of the number of times the user blinks at each time.

Note that, in FIG. 12, the horizontal axis illustrates time (time), and the vertical axis illustrates the number of times the user blinks in a period of one minute at each time.

In FIG. 12, a polygonal curve C51 illustrates the number of times the user blinks at each time, obtained based on the results of the open-close determination of the eyelid using the external temperature and the body temperature of the user. In this example, ordinarily, in a period from 0:00 to 06:00, which is the time during which a person is sleeping, and approaching 24:00, the number of times the user blinks is zero.

Conversely, in a time period in which the user is active, that is, in a period from 06:00 until 21:00, since the blinking is performed in a state in which the display device 11 is mounted to the user, the number of times the user blinks is a fixed number of times of approximately from 15 to 30.

Therefore, for example, when the number of blinks is within a predetermined range, the usage state determination unit 92 determines that the user is in the conscious state. Note that, in the same manner as the range RG11 of the pulse rate used in the usage state determination described above, for example, the range that is used in the usage state determination using the number of blinks may also be calculated based on the number of blinks that is measured in advance according to the guidance.

Here, description is given of performing the open-close determination of the eyelid based on the external temperature, and obtaining the number of blinks using the determination results. However, the number of blinks may be obtained based on the results of the open-close determination of the eyelid that is performed based on the pressure that is measured by the pressure detection unit 81, the received light signal that is output from the light receiving elements 54, and the like, in addition to obtaining the number of blinks based on the results of the open-close determination of the eyelid using the output of the temperature detection unit 82.

<Tear Detection Unit>

Description will be given of the tear detection unit 26.

Figure 13:
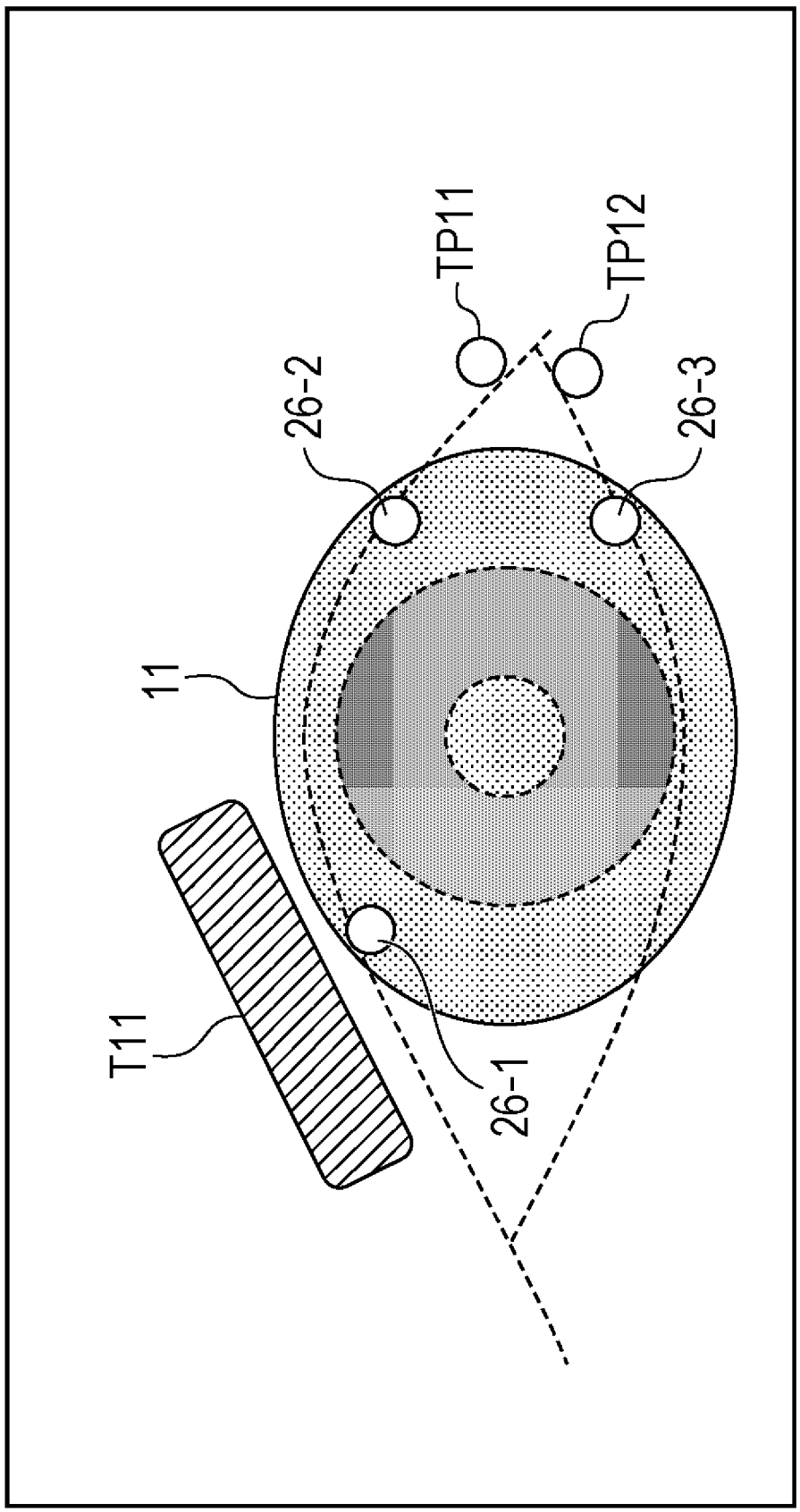
FIG. 13 is a diagram illustrating the disposition of tear detection units.

As illustrated in FIG. 13, for example, when the display device 11 is mounted on the user, the tear detection unit 26 is disposed so as to be positioned in the proximity of a tear gland T11 of the use, a tear point TP11 and a tear point TP12.

Note that, FIG. 13 illustrates a case when the user to which the display device 11 is mounted is viewed from the front, and the right side in the drawing is the center of the face of the user, and the left side in the drawing is the outside of the face of the user.

In this example, a tear detection unit 26-1 is provided on the top-left in the drawing of the surface of the eyeball side of the display device 11, that is, the top portion of the outside of the face. The tear gland T11 is in the proximity of the tear detection unit 26-1. A tear detection unit 26-2 and a tear detection unit 26-3 are provided, respectively, on the top-right and the bottom-right in the drawing of the surface of the eyeball side of the display device 11, that is, the top and the bottom of the center of the face.

A tear of the user is excreted from the tear gland T11 that is on the outside of the top eyelid of the user, and the tear is discharged from the tear point TP11 and the tear point TP12 which are close to the nose. The tear detection unit 26-1 detects the tear directly after the tear is excreted, and the tear detection unit 26-2 and the tear detection unit 26-3 detect a tear that travels over the eyeball of the user.

By providing the tear detection unit 26-1 on a portion that is closest to the tear gland T11 in this manner, the influence of interfering material other than tears is reduced, it is possible to detect more tears, and it is possible to more accurately perform the measurement of the tear excretion amount and the component analysis of the tears.

It is possible to precisely obtain the degree of dryness of the center of the eyeball of the surface of the pupil portion of the user based on the difference between the tear excretion amount that is detected by the tear detection unit 26-2 and the tear detection unit 26-3, and the tear excretion amount that is detected by the tear detection unit 26-1. Note that, the tear detection unit 26-2 and the tear detection unit 26-3 may not necessarily be provided.

At the time of usage of the contact lens type display device 11, in order not to damage the eyeball by reducing the friction with the eyeball of the user, it is necessary for there to be a film of tear between the eyeball and the display device 11.

For example, since it is known that when the eyelid of the user is closed for a long time such as when sleeping, the tear excretion amount is reduced, it is necessary to pay attention to a reduction in the tear excretion amount when using the display device 11 with the eyelid closed for a long period of time.

Therefore, when it is detected that the eyeball of the user is dry according to the dryness of the eyeball that is obtained from the tear excretion amount that is detected by the tear detection unit 26, the signal processing unit 27 applies a stimulus to the eye of the user, as appropriate, by controlling the driving of the display pixels 51 and changing the wavelength and the amount of light that is output from the display pixels 51. Accordingly, the generation of tears is promoted in relation to the user, and it is possible to prevent the drying of the eye.

Note that, the stimulus that is applied to the user in order to promote the generation of tears is not limited to a stimulus using light, and a stimulus may be applied to the eye using vibration by a vibration generating unit (not shown) in order to promote the generation of tears.

The amount of tears that are excreted from the user and the components of the tears are detected by each of the tear detection units 26. For example, the tear detection unit 26 includes a mechanism which samples a tear from the surface of the eyeball of the user to an analysis chamber via microscopic holes provided in the tear detection unit 26 using a micro-pump, and, in the analysis chamber, a functional block which analyses the components that are contained in the tear of the user that is samples. Furthermore, the tear detection unit 26 includes a mechanism which discharges the tear that is samples, subjected to component analysis, and the like.

However, it is generally known that a person excretes more tears when the person is in the conscious state than when the person is in the sleeping state. Therefore, it is possible to determine the usage state of the user based on the tear excretion amount that is detected by the tear detection unit 26.

The usage state determination unit 92 determines the usage state of the user by comparing the tear excretion amount of the user that is supplied from the tear detection unit 26 and a threshold that is determined in advance. Specifically, for example, when the tear excretion amount is greater than or equal to a threshold, the conscious state is determined.

Note that, the threshold that is compared with the tear excretion amount is obtained from the tear excretion amount of the time of the sleeping state and the tear excretion amount of the time of the conscious state, which are measured in advance for each user, for example.

In the component analysis of the tear in the tear detection unit 26, it is possible to obtain, not only the concentration (amount) of each component that is contained in the sampled tear, but also the initial reference concentration, the maximum concentration, the halved concentration, the maximum concentration attainment time, the half concentration attainment time, and the like of each component.

Note that, the appropriate component analysis method for the component analysis method of the tear may be determined from the classification of components such as proteins, hormones, and the like, the molecular weight, the quantitative precision, the temporal resolution, safety to the human body of derivatives which can be included in the display device 11, the necessary heat quantity for analysis, the ease of installation to the display device 11, and the like.

Specifically, for example, a plurality of methods that can be implemented in the display device 11 may be implemented, such as a method using enzymatic derivation and electrochemistry or fluorometry such as Ph variation caused by *bifidobacterium*, a glass electrode method (semiconductor), an electrophoresis method, an isoelectric focusing method, an immunoelectrophoresis method, Enzyme-Linked ImmunoSorbent Assay (ELISA), a synthetic substrate method, an amyloclastic method, a scattered turbidimetric method such as nephelometry, a fluorometric enzyme immunosorbent assay method (FETA), an enzyme immunosorbent assay method (EIA), an RIA method, and high performance liquid chromatography; a method of measuring a potential difference (potentiometry) using a −pH electrode of various types of voltammetry (voltammetry) such as cyclic and linear sweeping; a chemiluminescence method (chemiluminescence) which performs ppt (nM) level measurement in iron, manganese, or the like; an electron capture negative ion chemical ionization mass spectrometry method; and a method which uses a cortisol sensor chip in which cortisol antibodies are solidified on interdigital electrodes.

Figure 14:
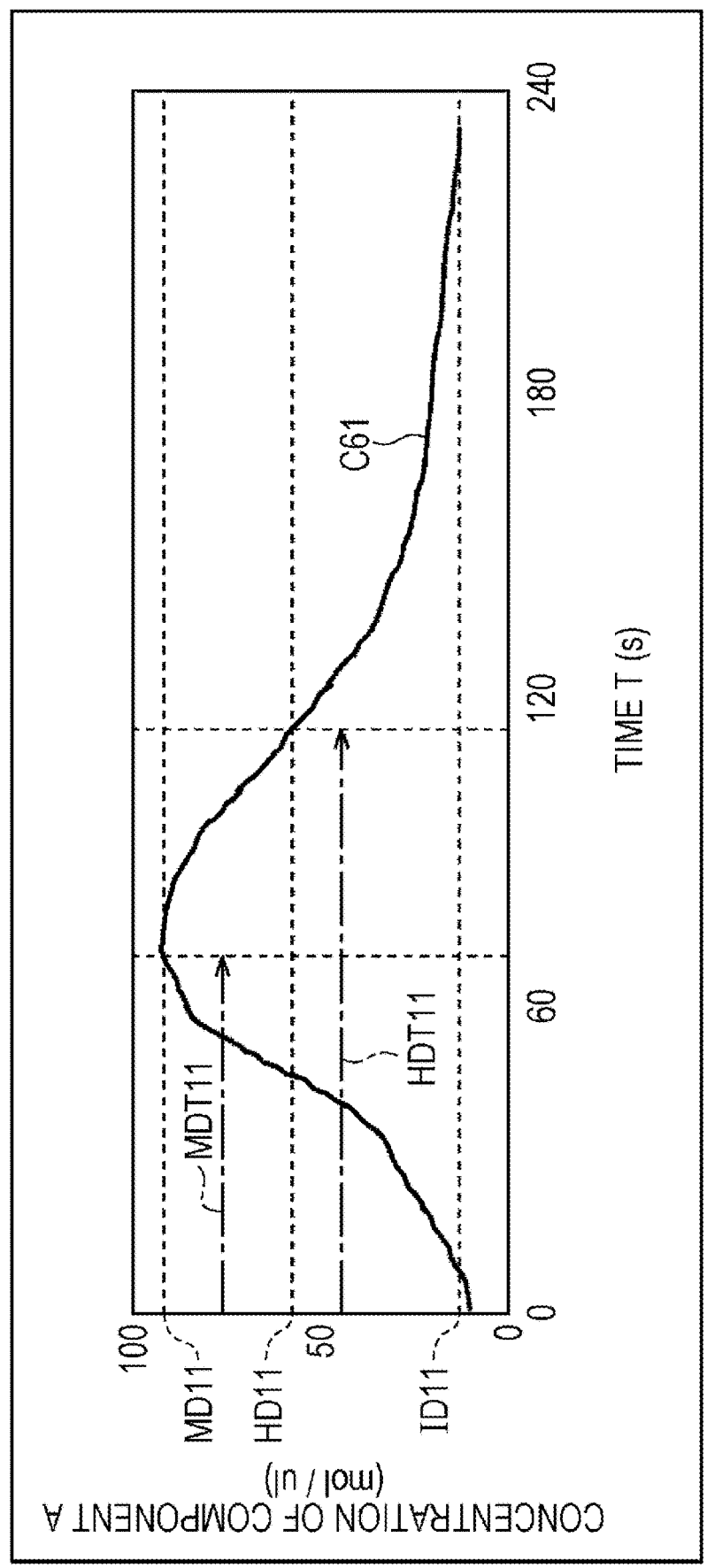
FIG. 14 is a diagram illustrating a tear component and a transition of time.

Here, FIG. 14 illustrates an example of the relationship between a predetermined component A that is contained in a tear that is sampled by the tear detection unit 26, and the transition of time of the component A. Note that, in FIG. 14, the horizontal axis illustrates time, and the vertical axis illustrates the concentration of the predetermined component A that is detected.

In this example, a curve C61 illustrates the concentration of the component A that is detected at each time.

As can be understood from the curve C61, the concentration of the component A is approximately an initial reference concentration ID11 directly after starting the detection; however, the concentration increases with time and reaches a maximum concentration MD11. After the concentration of the component A reaches the maximum concentration MD11, the concentration of the component A decreases with time, reaches the half concentration HD11, and subsequently decreases further and reaches the initial reference concentration ID11 again.

Here, the time from starting the detection of the concentration of the component A until the concentration reaches the maximum concentration MD11 is set as a maximum concentration attainment time MDT11, and the time from starting the detection of the concentration of the component A until the concentration reaches the half concentration HD11 is set as a half concentration attainment time HDT11 (a half-life).

When the tear detection unit 26 performs the measurement of the tear excretion amount and the component analysis of the tear, the tear detection unit 26 supplies the obtained tear excretion amount and the result of the component analysis to the signal processing unit 27. The signal processing unit 27 supplies the tear excretion amount and the result of the component analysis to the recording unit 83, and causes the recording unit 83 to record the tear excretion amount and the result of the component analysis, as necessary.

At this time, the tear excretion amount and the result of the component analysis are accumulated in the recording unit 83 according to the measurement time interval and the number of consecutive measurements of the tear detection unit 26. In particular, the data of the result of the component analysis that is accumulated in the recording unit 83 is data representing the relationship between the cumulative tear components and the transition of time.

Figure 15:
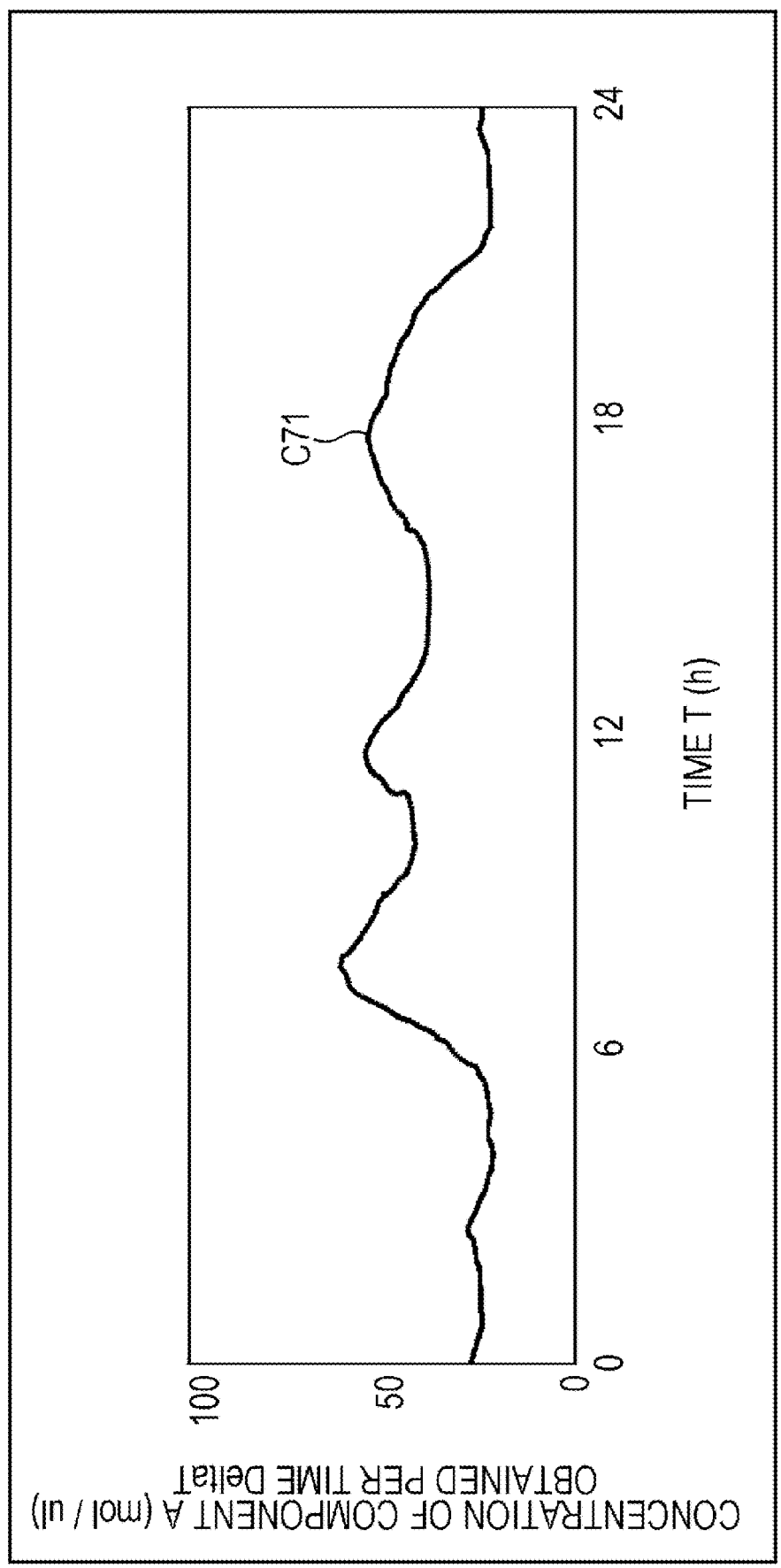
FIG. 15 is a diagram illustrating an accumulated tear component and the transition of time.

In other words, when the integrated value of the predetermined component A that is acquired during a predetermined time Delta T is obtained, the integrated value of the concentration of the component A at each time is obtained, as illustrated in FIG. 15, for example. Note that, in FIG. 15, the horizontal axis illustrates time, and the vertical axis illustrates the integrated value of the concentration of the component A that is acquired during the time Delta T.

In this example, a curve C71 illustrates the integrated value of the concentration of the component A that is acquired during the time Delta T at each time in one day, and it can be understood that the integrated value of the concentration of the component A changes with time. In the signal processing unit 27, a unit time concentration that increases in relation to the time Delta T in this manner is calculated as the concentration increase rate of the component A.

Note that, here, description is given of an example in which the integrated value of the concentration of the component A that is acquired during the time Delta T is obtained; however, the maximum value of the concentration of the component A that is acquired during the time Delta T may be obtained.

The signal processing unit 27 can specify the state of the living body of the user based on the results of the tear component analysis. This is because, together with changes in the state of the living body such as the emotions of the user, the content of each component that is contained in the tear that is excreted from the user changes with time.

It is possible to use not only the concentration of each component that is contained in the tear, but also the maximum concentration, the maximum concentration attainment time, the concentration increase rate, and the like in the specification of the state of the living body of the user.

Therefore, three tears, tears of a state that mainly protects the eye, stimulation tears, and emotion tears are defined as states of tears that change according to the state of the living body of the user.

First, for a tear of the state that protects the eye, the user is in an ordinary state, and the tear is excreted when there are not any particularly large undulations in emotion. That is, the tear is for forming a film of tear on the eyeball together with blinking and protect the eye.

The stimulation tears are tears that are excreted when the user is in a short term painful state such as when foreign matter enters the eye, or a stimulus is received such as allyl sulfide of an onion, that is, tears for protecting against reflex stimulation.

Emotion tears are tears that are excreted with the exhibition of emotion such as happy times or sad times. Examples of such emotion tears include continuous tears and stress tears.

Continuous tears are tears which are excreted in a state in which pain continually occurs in the user. Therefore, for example, when a state in which the user is in short term pain continues of a long period, the tears that are excreted from the user change from stimulation tears to continuous tears.

Stress tears are tears which caused by stress and are excreted in a state in which the user continuously generates deep sorrow or concern.

The signal processing unit 27 determines whether tear that are excreted from the user are tears of a state that protects the eye, stimulation tears, or emotion tears based on the tear analysis results that are supplied from the tear detection unit 26 or the analysis results of the tear that are recorded in the recording unit 83.

For example, stimulation tears contain much globulin, albumin, lactoferrin, substance P, and the like as components.

Therefore, for example, when, as a result of the component analysis of the tear, lactoferrin is detected from the tear of the user and the lactoferrin has increased over a short period, the signal processing unit 27 determines that the tear that is excreted from the user is a stimulation tear. That is, the state of the living body of the user is determined to be a state in which short term pain is present.

A continuous tear, which is an example of the emotion tear, contains much lactoferrin, substance P, and the like as components.

Therefore, for example, when, as a result of the component analysis of the tear, lactoferrin is detected from the tear of the user and the period over which the lactoferrin is increased is maintained for a long period, the signal processing unit 27 determines that the tear is the continuous tear of the emotion tears. Note that, for example, when the stimulation tears continue to be detected for a fixed period or longer, it may be determined that the continuous tears are detected.

Furthermore, a stress tear, which is an example of the emotion tear, contains much amylase, adrenocorticotropic hormone, corticotropin-releasing hormone, and the like.

The signal processing unit 27 specifies the state of the tear that is sampled from the user at the present time by comparing the concentration of each component that is detected from the tear by the component analysis, for example, and a threshold that is obtained in advance, and takes the state of the tears until this point into consideration, an determines the state of the living body of the user from the specified results.

Note that, here, description is given of an example in which the state of the living body of the user is determined based on the results of the component analysis of the tears; however, in addition, presentation information such as images, audio, text, and context, input information that is input by the user or the like such as voice, text, and context, component analysis results of a substance such as sweat that is obtained from another part of the user than the eye.

For example, when an image is displayed on the display elements 55, the signal processing unit 27 performs scene recognition on the image, using the image that is being displayed as the presentation information, and determines the state of the living body of the user based on the results of the scene recognition and the results of the tear component analysis.

For example, when input of the text information or the like is performed by the user, the signal processing unit 27 extracts characters indicating the emotion or the like of the user from the text information, using the text information that is input as the input information, and determines the state of the living body of the user based on the extraction results and the results of the tear component analysis.

For example, when the component analysis results of a substance such as sweat which is obtained from a specific part of the user are supplied to the display device 11 from an auxiliary sensor or the like that is connected by wireless or the like, the signal processing unit 27 determines the state of the living body of the user based on the results of the component analysis of the substance that are supplied and the results of the component analysis of the tears.

Note that, the specific part at which the detection of the sweat or the like is performed is set as a portion such as, for example, a palm of a hand, a base of a thumb, under an armpit, and a neck, and the detection or component analysis of sweat is performed using sweat sensors which are provided in one or a plurality of the parts. For example, the results of the component analysis of the sweat or the like are transmitted by wireless from a device such as a sweat sensor to be received by the signal antenna 23, and are supplied to the signal processing unit 27. Here, description will be given of an example in which the component analysis of the sweat is performed; however, in addition, any substance may be a component analysis target, such as saliva in the oral cavity of the user, urine that is obtained from a urethral catheter, and other waste products.

The signal processing unit 27 is not limited to using one of the input information and the results of the component analysis of sweat or the like, and may determine the state of the living body of the user using some of this information and the results of the tear component analysis. In this manner, it is possible to specify the state of the living body of the user with higher precision by using other auxiliary information in addition to the results of the tear component analysis.

If it is possible to specify the state of the living body such as the emotion of the user, it is possible to execute a process according to the state of the living body.

For example, when the state of the emotion of the user is specified as the state of the living body of the user, it is possible to cause the display region 21 to display an image matched to the specified emotion. Specifically, for example, when the user sees an unpleasant dream while sleeping, that is, in the sleeping state, a reaction such as sweating, a rise in pulse, and tension of the body is seen in the human body.

Therefore, when it is determined that the user is viewing an unpleasant dream from the information relating to the living body of the user such as the emotional state of the user, and the pulse information, the signal processing unit 27 causes the display region 21 to display a video that serves to calm the feelings, and alleviates the unpleasant dream.

Note that, for example, if a component which suppresses a component that is generated in the stress tear state is detected by the component analysis of the tear that is sampled from the user, it is possible to determine whether the content that is presented to the user by the display device 11 has the effect of suppressing stress for the user.

For example, if a component which generates pleasure, or a component which suppresses the component which generates pleasure is detected by the component analysis of the tear, it is possible to determine whether the content that is presented to the user by the display device 11 is effective, in the same manner.

In the manner described above, the display device 11 can detect living body information such as the pulse information, emotion information, and body temperature in addition to determining the opening and closing of the eyelid and the usage state of the user.

Therefore, the display device 11 realizes the various functions using the determination results and the detection results, and it is possible to improve the usability of the display device 11.

For example, when the user is in the sleeping state and the eyelid of the user is closed, the signal processing unit 27 can urge to user to awaken by causing the display pixels 51 to emit light corresponding to a waking time that is set in advance, directly irradiate the retina of the user with light, display video, or the like. That is, it is possible to realize an alarm clock function. At this time, when a strong light is emitted, since the stimulus is strong and the burden to the human body is great, the user is urged to awaken using an appropriate amount of light emission and light emission rhythm to lead the user to consciousness.

For example, when the sleeping state is determined and conditions that are set in advance are met, the signal processing unit 27 can present information to the retina during sleep by displaying prepared information, and promote information such as learning. That is, it is possible to realize a sleep learning function. It is possible to present information that alleviates symptoms in medical treatment using a similar method.

When the sleeping state is determined and conditions that are set in advance are met, the signal processing unit 27 displays video or information, which is prepared in advance, relating directly or indirectly to a dream that user wishes to view on the display region 21. Accordingly, the information or video is presented to the retina while the user is asleep, and it is possible to promote the ability of the user to view a desired dream. That is, it is possible to perform dream guidance.

In the same manner as a case of a contact lens for diopter adjustment, when the display device 11 is mounted to the user, in the conscious state, a thin layer of tear is formed between the display device 11 and the eyeball by a tear that is excreted from the user, and the eyeball is protected. However, there is a case in which the excretion of tears decreases when sleeping such as retiring to sleep.

Therefore, when the display device 11 is continuously mounted to the eyeball of the user, the protective layer created by tears between the eyeball and the display device 11 decreases, and there is a likelihood that the eyeball will be damaged. Therefore, when the protective layer created by the tears decreases, the signal processing unit 27 applies a stimulus to the eye to an extent that does not apply discomfort by periodically changing the wavelength or the amount of light that is output from the display pixels 51 of the display device 11, promotes the generation of tears, and it is possible to ensure that the protective layer that is created by tears is supplied. A configuration may be adopted in which a vibration generating unit is provided in the display device 11, a stimulus is applied to the eyeball or the eyelid using vibration to an extent that does not apply discomfort, and the generation of tears is promoted.

<Description of Display Drive Process>

Next, description will be given an example of the specific operations of the display device 11.

Figure 16:
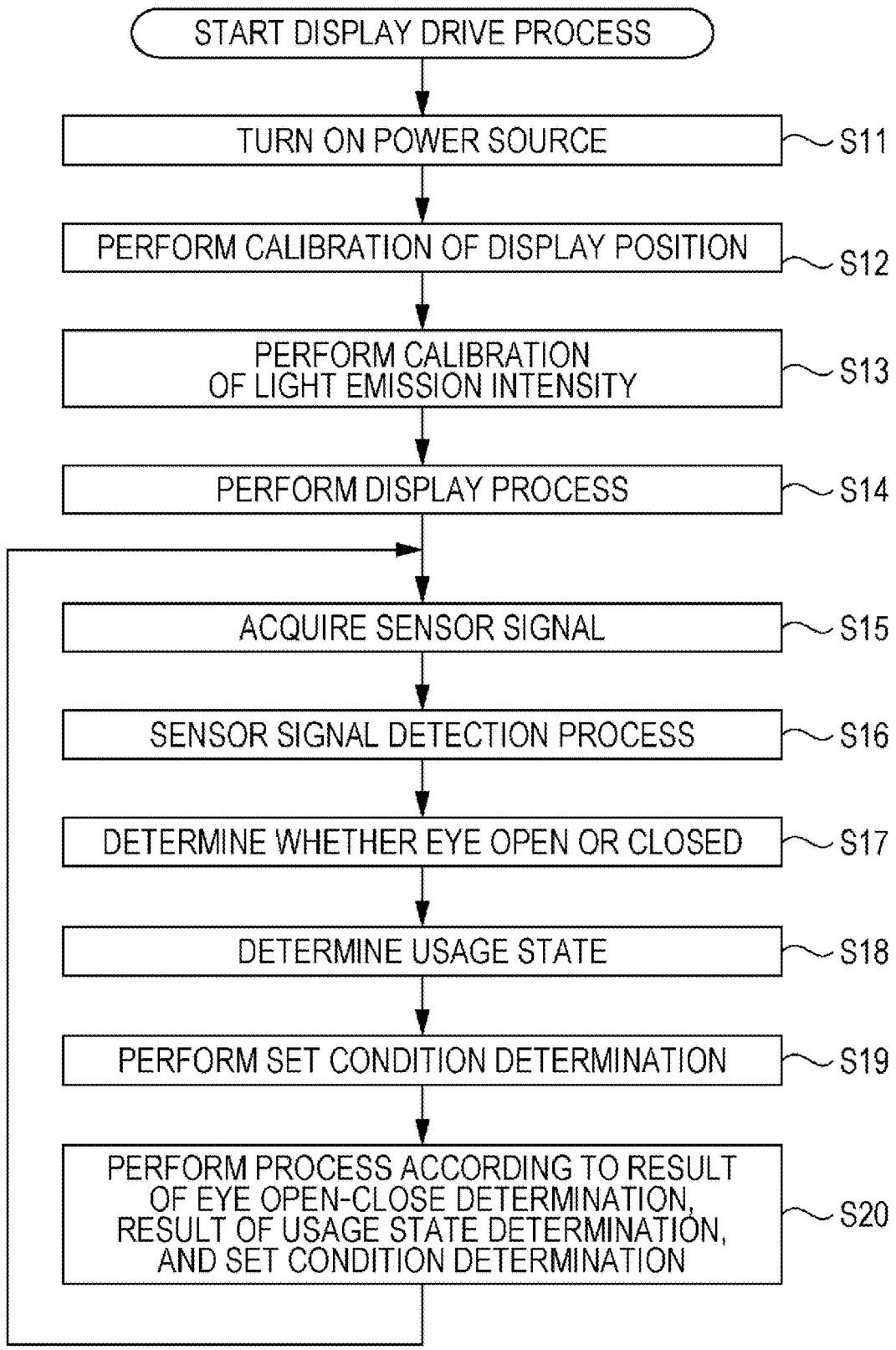
FIG. 16 is a flowchart illustrating a display drive process.

Hereinafter, description will be given of the display drive process that is performed by the display device 11 with reference to the flowchart of FIG. 16.

The display drive process is started in the display device 11 when it is detected that the display device 11 is mounted to the eyeball of the user. For example, when a comparatively great pressure is detected by the pressure detection unit 81, or when it is detected that the difference between the temperature of the surface of the eyeball of the user and the external temperature is a predetermined value or greater by the temperature detection unit 82, it is detected that the display device 11 is mounted to the eyeball of the user.

In step S11, the drive control unit 93 turns the power source on. In other words, the drive control unit 93 controls the electrical generation unit 24 and causes the electrical generation unit 24 to supply power to each part of the display device 11. Accordingly, for example, from a state in which the power is supplied to a portion of the display device 11, a state is assumed in which the power is supplied to all of the display device 11.

In step S12, the signal processing unit 27 performs calibration of the display position.

For example, the drive control unit 93 of the signal processing unit 27 supplies a positioning image for the calibration to the display element drive unit 28, causes the display pixels 51 to emit light, and causes the display region 21 to display several positioning images. The user pays attention to the positioning image and performs a selection operation such as closing the eyelid, as appropriate, according to audio, guidance or the like that is displayed on the display region 21.

The drive control unit 93 controls the display element drive unit 28 to cause the display pixels 51 to emit light. That is, the display pixels 51 are caused to output light for line of sight detection. Therefore, a received light signal corresponding to the amount of received light, which is the light that is output from the display pixels 51 and reflected by the surface of the eyeball of the user, is supplied from the light receiving elements 52 to the signal processing unit 27.

The signal processing unit 27 detects the line of sight position of the user based on the received light signal that is supplied from the light receiving elements 52, and corrects the display position of the image in the display region 21 by the amount of shifting that is present between the line of sight position and the positioning image.

In step S13, the signal processing unit 27 performs calibration of the light emission intensity.

For example, the drive control unit 93 of the signal processing unit 27 controls the display element drive unit 28 to cause the display pixels 51 to emit light. Therefore, a received light signal corresponding to the amount of received light, which is the light that is output from the display pixels 51 and reflected by the surface of the eyeball of the user, is supplied from the light receiving elements 52 to the signal processing unit 27.

The signal processing unit 27 adjusts the light emission intensity of the display pixels 51 such that the intensity of the light that is output from the display pixels 51 is an appropriate intensity that does not excessively stimulate the eye of the user based on the received light signal that is supplied from the light receiving elements 52. The signal processing unit 27 adjusts the light emission intensity of the light emitting elements 53 in the same manner. As necessary, the signal processing unit 27 performs calibration of the detection position or the like of the light using the light receiving elements 52 and the light receiving elements 54.

In step S14, the drive control unit 93 performs a display process. For example, the drive control unit 93 controls the display element drive unit 28 to cause the display pixels 51 to emit light, and causes the display pixels 51 to display a predetermined image or information. Accordingly, for example, a user interface or the like is displayed on the display region 21.

When the display process is performed, the pressure detection unit 81, the posture detection unit 25, the tear detection unit 26, and the temperature detection unit 82 start the detection of the pressure, the posture, the tears, the external temperature, the temperature of the surface of the eyeball, and the like. The light emitting elements 53 also emit light, and the light receiving elements 54 also start the detection of the light from the light emitting elements 53.

In step S15, the signal processing unit 27 acquires the sensor signals that are output from each sensor. In other words, the signal processing unit 27 acquires the outputs from the pressure detection unit 81, the posture detection unit 25, the tear detection unit 26, the temperature detection unit 82, the light receiving elements 52, and the light receiving elements 54.

In step S16, the signal processing unit 27 performs the sensor signal determination process based on the various sensor signals that are acquired in the process of step S15.

Specifically, for example, the signal processing unit 27 detects the posture of the user based on the signal that is output from the posture detection unit 25, obtains the pulse information of the user based on the output from the pressure detection unit 81, and the like.

In step S17, the open-close determination unit 91 determines the opening and closing of the eyelid of the user based on at least one of the received light signals from the light receiving elements 54, a signal indicating the pressure that is supplied from the pressure detection unit 81, the external temperature that is supplied from the temperature detection unit 82, or the like.

In step S18, the usage state determination unit 92 determines the usage state of the user based on the pulse information of the user, the posture, the tear excretion amount, and the like. In other words, it is determined whether the user is in the sleeping state or in the conscious state.

In step S19, the signal processing unit 27 performs set condition determination.

For example, when a specific condition is satisfied, such as that the user is in a specific emotional state, when a process corresponding to the condition is set, in advance, to be executed, the signal processing unit 27 determines whether or not the conditions that are set by the user are satisfied.

In step S20, the signal processing unit 27 performs a process according to the determination results based on the results of the open-close determination of the eyelid, the results of the usage state determination, and the results of the set condition determination. When the processes according to each of the determination results are performed, subsequently, the process returns to step S15, and the processes that are described above are performed again.

As described above, the display device 11 performs the various processes according to the results of the open-close determination of the eyelid and the usage state determination. In this manner, by performing the processes based on the information that is obtained in regard to the user to which the display device 11 is mounted, it is possible to perform the appropriate processes without operation by the user being necessary.

<Description of Display Control Process with Regard to Conscious State Mode>

However, the display device 11 has a conscious state mode in which the control of the display to the display region 21 and the like is performed when the user is in the conscious state, and a sleeping state mode in which the control of the display to the display region 21 and the like is performed when the user is in the sleeping state. In other words, in a state in which the display device 11 is operating, the conscious state mode is transitioned to when the user is in the conscious state, the sleeping state mode is transitioned to when the user is in the sleeping state, and the display control and the like is performed in each mode.

Hereinafter, description will be given of the processes that are performed by the display device 11 in a case of the conscious state mode, and in a case of the sleeping state mode, respectively, corresponding to the processes of step S15 to step S20 of FIG. 16.

First, description will be given of the display control process that is performed in the case of the conscious state mode with reference to the flowchart of FIG. 17. The display control process in the conscious state mode that will be described with reference to FIG. 17 describes the processes of step S15 to step S20 of FIG. 16, which are performed in the case of the conscious state mode, in more detail.

In step S51, the signal processing unit 27 acquires the sensor signals. In other words, the signal processing unit 27 acquires the received light signals from the light receiving elements 52, the received light signals from the light receiving elements 54, the signal indicating the pressure from the pressure detection unit 81, the signal indicating the posture and the movement from the posture detection unit 25, the tear excretion amount and the component analysis results from the tear detection unit 26, and the signal indicating the external temperature and the temperature of the surface of the eyeball from the temperature detection unit 82.

In step S52, the signal processing unit 27 performs a posture determination process.

For example, the signal processing unit 27 determines which posture the user is in, such as the standing position, the sitting position, the supine position, the Sims' position, or the prone position based on the angles or the like of the vertical reference plane and the horizontal reference plane in relation to the ground supplied from the posture detection unit 25.

In step S53, the signal processing unit 27 performs a body temperature determination process.

For example, the signal processing unit 27 calculates the body temperature of the user from the difference between the temperature of the surface of the eyeball that is supplied from the temperature detection unit 82 and the reference body temperature.

In step S54, the signal processing unit 27 performs a tear excretion amount determination process. Specifically, the signal processing unit 27 sets the measurement results of the tear excretion amount that are supplied from the tear detection unit 26 to the tear excretion amount of the user at the present time.

The signal processing unit 27 determines the state of the tears of the user, that is, the state of the living body such as the emotion or the like of the user based on the tear excretion amount and the analysis results that are supplied from the tear detection unit 26.

In step S55, the signal processing unit 27 detects the pulse rate.

For example, the signal processing unit 27 determines the pulse information and the blood flow information based on the received light signals that are supplied from the light receiving elements 52, and calculates the pulse rate of the user from the obtained pulse information and blood flow information.

Note that, the signal processing unit 27 may calculate the pulse rate of the user in the same manner as in the case of the light receiving elements 52 based on the received light signals that are supplied from the light receiving elements 54 in the state in which the eyelid of the user is closed. The signal processing unit 27 may obtain the pulse information based on the signal indicating the pressure that is applied to the display device 11 and is supplied from the pressure detection unit 81 in the state in which the eyelid of the user is closed, and calculate the pulse rate from the pulse information.

The processes of step S52 to step S55 described above may be performed in any order, and a portion of the processes may be performed as necessary. A portion or all of the processes of step S52 to step S55 may be performed in parallel.

In step S56, the open-close determination unit 91 performs the open-close determination of the eyelid of the user.

For example, the open-close determination unit 91 causes the light emitting elements 53 to emit light, and determines whether the eyelid of the user is open based on the received light signals that are supplied from the light receiving elements 54. For example, when the light receiving elements 54 receive the light for eyelid open-close detection that is output from the light emitting elements 53, it is determined that the eyelid of the user is closed when the amount of received light that is indicated by the received light signals from the light receiving elements 54 is greater than or equal to a predetermined threshold.

For example, the open-close determination unit 91 performs the open-close determination of the eyelid of the user based on the signal indicating the pressure that is applied to the display device 11 and is supplied from the pressure detection unit 81. Specifically, for example, when the pressure that is detected by the pressure detection unit 81 is greater than or equal to the threshold, it is determined that the eyelid of the user is closed.

For example, the open-close determination unit 91 performs the open-close determination of the eyelid of the user based on living body information that is obtained from the user, for example, manner in which the external temperature that is detected by the temperature detection unit 82 rises. Specifically, for example, when the external temperature rises from a predetermined temperature that serves as a reference, it is determined that the eyelid is closed. When the amount of change in the external temperature in a fixed time is less than or equal to a predetermined threshold, it may be determined that the eyelid of the user is closed.

Note that, the open-close determination of the eyelid may be performed using one of determination based on the received light signals, determination based on the pressure, or determination based on the external temperature, and the final determination may be performed by performing a plurality of the determination processes using the majority decision or the like of the determination results. For example, when a majority decision is performed, when two or more of the determination results of the determination result based on the received light signals, the determination result based on the pressure, and the determination result based on the external temperature are determination results indicating that the eyelid of the user is closed, it is determined that the eyelid of the user is closed as the final determination result.

In step S57, the signal processing unit 27 performs the closed-eyelid time determination process. In other words, the signal processing unit 27 calculates the closed-eyelid time indicating the time that the eyelid of the user is continually closed based on the proximal results of the open-close determination of the eyelid of the user.

The signal processing unit 27 also calculates the number of blinks of the user based on the proximal results of the open-close determination of the eyelid of the user.

In step S58, the usage state determination unit 92 performs the usage state determination process.

For example, the usage state determination unit 92 determines whether the user is in the conscious state or in the sleeping state based on the pulse rate that is obtained in step S55.

For example, the usage state determination unit 92 determines the usage state of the user based on the result of the posture determination that is obtained in the process of step S52. Specifically, for example, when the posture of the user is one in which the body is lain down for a fixed time or longer, and, no action is detected by the posture detection unit 25, the sleeping state is determined.

For example, the usage state determination unit 92 determines the usage state based on the difference between the body temperature of the user and the external temperature that is obtained in the process of step S53. In this case, for example, when the difference between the body temperature and the external temperature is greater than or equal to the threshold, it is determined that the user is in the conscious state.

For example, the usage state determination unit 92 determines the usage state based on the number of blinks of the user that is calculated in the process of step S57. Specifically, for example, when the number of blinks is within a predetermined range that is determined in advance, it is determined that the user is in the conscious state.

For example, the usage state determination unit 92 determines the usage state by comparing the tear excretion amount and the threshold that are obtained in the process of step S54. Specifically, for example, when the tear excretion amount is greater than or equal to a threshold, the conscious state is determined.

Note that, the usage state determination may be performed based on information relating to (the living body of) the user such as at least one of the pulse rate, the results of the posture determination, the difference between the body temperature and the external temperature, the number of blinks, and the tear excretion amount, and the final determination may be performed by performing a plurality of the determination processes using the majority decision or the like of the determination results. For example, when the final determination is performed by majority decision, when a predetermined number or more determination results are obtained indicating the conscious state, the final determination result is determined to be the conscious state.

The final usage state determination may be determined based on one or a plurality of usage state determination results and the results of the open-close determination of the eyelid.

Specifically, for example, when the eyelid is determined to be open by the open-close determination of the eyelid, it is assumed that the user is in the conscious state. Even when it is determined that the eyelid of the user is closed, when the determination result indicating that the user is in the conscious state is obtained according to one or a plurality of the usage state determination results, the final usage state determination result is also assumed to be the conscious state.

In step S59, the signal processing unit 27 determines whether or not the usage state determination result in step S58 is the conscious state.

In step S59, when the conscious state is determined, in step S60, the signal processing unit 27 continues the display state at the present time.

In other words, when the user is in the conscious state, since the conscious state mode is set and the display control is performed, the signal processing unit 27 causes the display region 21 to display the image and the like as described hereto.

In step S61, the signal processing unit 27 determines whether or not the eyelid of the user is open as a result of the open-close determination of the eyelid.

In Step S61, when it is determined that the eyelid is open, the signal processing unit 27 determines whether or not to apply the set condition in step S62.

For example, as a set condition that is specified in advance by the user, it will be assumed that a condition in which the eyelid of the user is open and the display process is being performed in an augmented reality (AR) mode (augmented reality) on the display region 21 in a specific posture is defined as the set condition. When the set condition is satisfied, it is assumed that it is specified that the guidance function is executed.

In such a case, the signal processing unit 27 determines whether or not the set condition is satisfied based on the result of the posture determination of step S52, the determination result of step S61, and the display process that is being performed at present. When it is determined that the set condition is satisfied, the signal processing unit 27 determines that the set condition is to be applied in step S62.

In step S62, when it is determined that the set condition is not to be applied, the process returns to step S51, and the processes that are described above are performed again.

Conversely, in step S62, when it is determined that the set condition is to be applied, the signal processing unit 27 performs the display control corresponding to the set condition in step S63.

For example, when the set condition in which the eyelid of the user is open and the display process is being performed in the AR mode on the display region 21 in a specific posture is applied, it is assumed that the execution of the guidance function is specified. In such a case, the drive control unit 93 of the signal processing unit 27 causes the display element drive unit 28 to drive, causes the display pixels 51 to display the guidance or the like, and executes the guidance function.

In addition, for example, various processes may be performed, such as an information presentation process or the execution of the AR mode, as the operation that is set in advance in regard to each set condition. In this case, since the eyelid of the user is open, the operation that is set in advance may be an operation that is appropriate to perform when the eyelid of the user is open.

In step S63, when the display control corresponding to the set condition is performed, subsequently, the process returns to step S51, and the processes that are described above are performed again.

In step S59, when the usage state is determined not to be the conscious state, that is, is determined to be the sleeping state, in step S64, the drive control unit 93 controls the display element drive unit 28 to cause the display region 21 to stop the display of the image. The drive control unit 93 controls the electrical generation unit 24 as necessary, causes the power supply to a specific block of the display device 11, for example, to the display element drive unit 28, or the like, and sets a sleep state.

Figure 18:
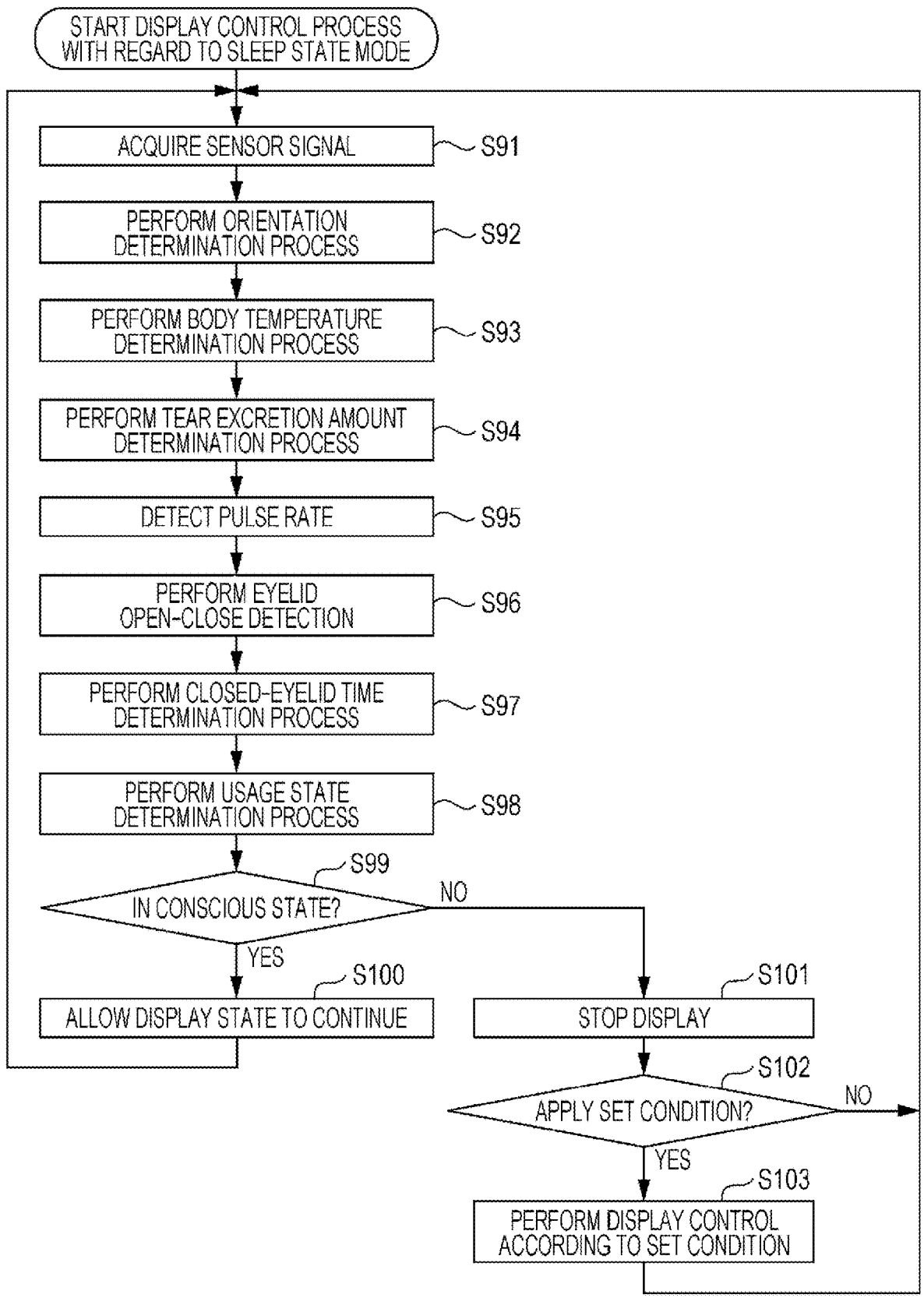
FIG. 18 is a flowchart illustrating a display control process with regard to a sleeping state mode.

When the display device 11 is set to the sleep state, subsequently, the process returns to step S51, and the processes described above are performed again. Note that, more specifically, when the sleeping state is determined, the display control process transitions from the conscious state mode to the sleeping state mode, and the display control process with regard to the sleeping state mode that is described below with reference to FIG. 18 is executed.

In Step S61, when it is determined that the eyelid is not open, the signal processing unit 27 determines whether or not to apply the set condition in step S65.

In step S65, when it is determined that the set condition is not to be applied, the process returns to step S51, and the processes that are described above are performed again.

Meanwhile, in step S65, when it is determined that the set condition is to be applied, in step S66, the signal processing unit 27 performs the display control corresponding to the set condition.

For example, the operation of a video mode in which a moving image is reproduces, the operation of a meditation mode in which music for meditation is reproduced, the operation of a game mode in which a game function is executed, and the like are performed as the modes that are set in advance in regard to the set condition. Note that, the reproduction of audio is performed by transmitting a command to an external speaker using the signal antenna 23, for example.

In step S66, when the display control corresponding to the set condition is performed, subsequently, the process returns to step S51, and the processes that are described above are performed again.

In the manner described above, the display device 11 performs the open-close determination of the eyelid of the user using at least one of the items of living body information relating to the user such as the temperature (the external temperature) of the eyelid of the user, the amount of light that is received from light that is reflected from the eyelid of the user or the outside, and the pressure that is applied to the display device 11. Accordingly, it is possible to detect the opening and closing of the eyelid of the user at high precision using a simpler configuration, that is, without an external device other than the display device 11 being particularly necessary.

The display device 11 determines the usage state of the user using living body information (information relating to biology) such as one or a plurality of the pulse rate, the posture, the body temperature, the number of blinks, and the tear excretion amount of the user. Accordingly, it is possible to specify the usage state of the user at high precision using a simpler configuration. In particular, if the usage state is determined by combining the single or plural items of living body information and the results of the open-close determination of the eyelid, it is possible to further increase the determination precision of the usage state.

For example, in the display device 11, there is no case in which the user is erroneously determined to be in the sleeping state, even when the user is in the conscious state and blinks or temporarily closes the eyelid when in the standing position or the sitting position posture. For example, in the display device 11, even if the user closes the eyelid for a long time in the conscious state, information presentation and the like continues to be performed without the user being erroneously determined to be in the sleeping state.

In the display device 11, since it is possible to distinguish, at high precision, a state in which the user is in a decubitus position posture in the conscious state, a state in which the eyelid of the user is closed in the sleeping state, and the like, it is possible to automatically or semi-automatically present information that is appropriate to the state of the user, and it is possible to improve usability.

<Description of Display Control Process with Regard to Sleeping State Mode>

Next, description will be given of the processes that are performed by the display device 11 in a case of the sleeping state mode, corresponding to the processes of step S15 to step S20 of FIG. 16.

In other words, hereinafter, description will be given of the display control process that is performed in the sleeping state mode with reference to the flowchart of FIG. 18. The display control process in the sleeping state mode that will be described with reference to FIG. 18 describes the processes of step S15 to step S20 of FIG. 16, which are performed in the case of the sleeping state mode, in more detail.

Figure 17:
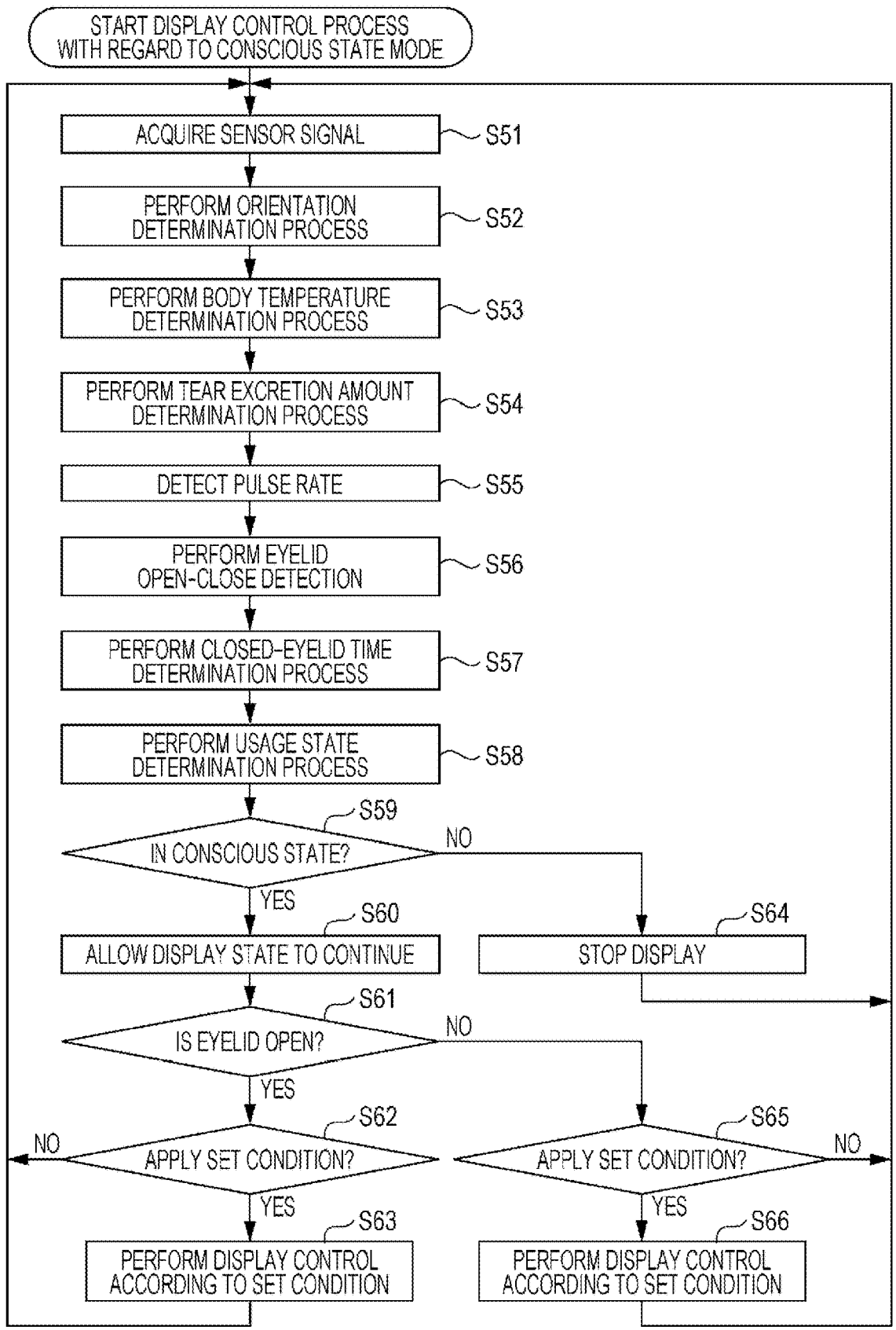
FIG. 17 is a flowchart illustrating a display control process with regard to a conscious state mode.

Note that, since the processes of step S91 to step S98 are the same as the processes of step S51 to step S58 of FIG. 17, description thereof will be omitted.

In step S99, the signal processing unit 27 determines whether or not the result of the usage state determination in step S98 is the conscious state. Note that, in more detail, the processes of step S51 to step S59 of FIG. 17 and the processes of step S91 to step S99 of FIG. 18 are the same processes, and commonly performed in the conscious state mode and in the sleeping state mode.

In step S99, when the conscious state is determined, in step S100, the signal processing unit 27 continues the display state at the present time and the process returns to step S91. Subsequently, the processes that are described above are performed again.

In other words, when the conscious state is determined in step S99, a transition occurs from the sleeping state to the conscious state. More specifically, when the conscious state is transitioned to, that is, when the process of step S100 is performed, the processes of step S61 to step S63 described in FIG. 17 and the processes of step S65 and step S66 are performed.

Conversely, in step S99, when the conscious state is not determined, that is, the sleeping state is determined, the sleeping state mode is set, the process proceeds to step S101, and the drive control unit 93 controls the display element drive unit 28 to cause the display region 21 to stop the display of the image. The drive control unit 93 controls the electrical generation unit 24 as necessary, causes the power supply to a specific block of the display device 11, for example, to the display element drive unit 28, or the like, and sets a sleep state.

In Step S102, the signal processing unit 27 determines whether or not to apply the set condition.

In step S102, when it is determined that the set condition is not to be applied, the process returns to step S91, and the processes that are described above are performed again.

Meanwhile, in step S102, when it is determined that the set condition is to be applied, in step S103, the signal processing unit 27 performs the display control corresponding to the set condition.

For example, in the case of a set condition in which the user is in the sleeping state and the state of the tear is a stress tear, it is assumed that the reproduction of video with a relaxing effect is specified by the user.

In such a case, since the user is in the sleeping state and the state of the tear is the stress tear, when it is determined that the set condition is applied in the process of step S102, the drive control unit 93 of the signal processing unit 27 drives the display element drive unit 28 to cause the display pixels 51 to display video.

In addition, as an operation that is set in advance in regard to each set condition, for example, when in the sleeping state, at ordinary times display is stopped since the display of information is not necessary; however, an alarm which promotes a comfortable awakening may be performed by gradually raising the luminosity level of the display in accordance with a waking time that is set in advance.

For example, when the excretion of tears becomes necessary due to the fact that, during sleep, the excretion of tears is reduced, an operation such as a stimulation operation which promotes excretion, the presentation of guidance video which promotes dreams, the presentation of video which promotes a learning effect, or the like may be executed as a pre-set operation.

In step S103, when the display control corresponding to the set condition is performed, subsequently, the process returns to step S91, and the processes that are described above are performed again. Note that, more specifically, in the display control process that is described with reference to FIG. 17, when the sleeping state is determined in step S59, the sleeping state mode is transitioned to, and, after the process of step S64, the processes of step S102 and step S103 of FIG. 18 are performed.

In the manner described above, the display device 11 performs the open-close determination of the eyelid of the user using at least one of the items of living body information relating to the user such as the temperature (the external temperature) of the eyelid of the user, the amount of light that is received from light that is reflected from the eyelid of the user or the outside, and the pressure that is applied to the display device 11.

Accordingly, even in the same of the sleeping state mode, it is possible to detect the opening and closing of the eyelid of the user at high precision using a simpler configuration. Since the display device 11 determines the usage state of the user using single or plural items of living body information, it is possible to specify the usage state at high precision using a simpler configuration.

Second Embodiment

<Configuration Example of Contact Lens Type Display Device>

Note that, the above description relates to within the display region 21, and it is described that the light emitting elements 53 and the light receiving elements 54 for eyelid open-close detection are provided on the eyeball side of the inside of the display device 11; however, the light emitting element 53 and the light receiving element 54 may be provided in any position if it is possible to perform the open-close determination of the eyelid.

For example, the light emitting element 53 and the light receiving element 54 may be provided on the outside of the display region 21 and in a position of the outside of the inside of the display device 11.

Figure 19:
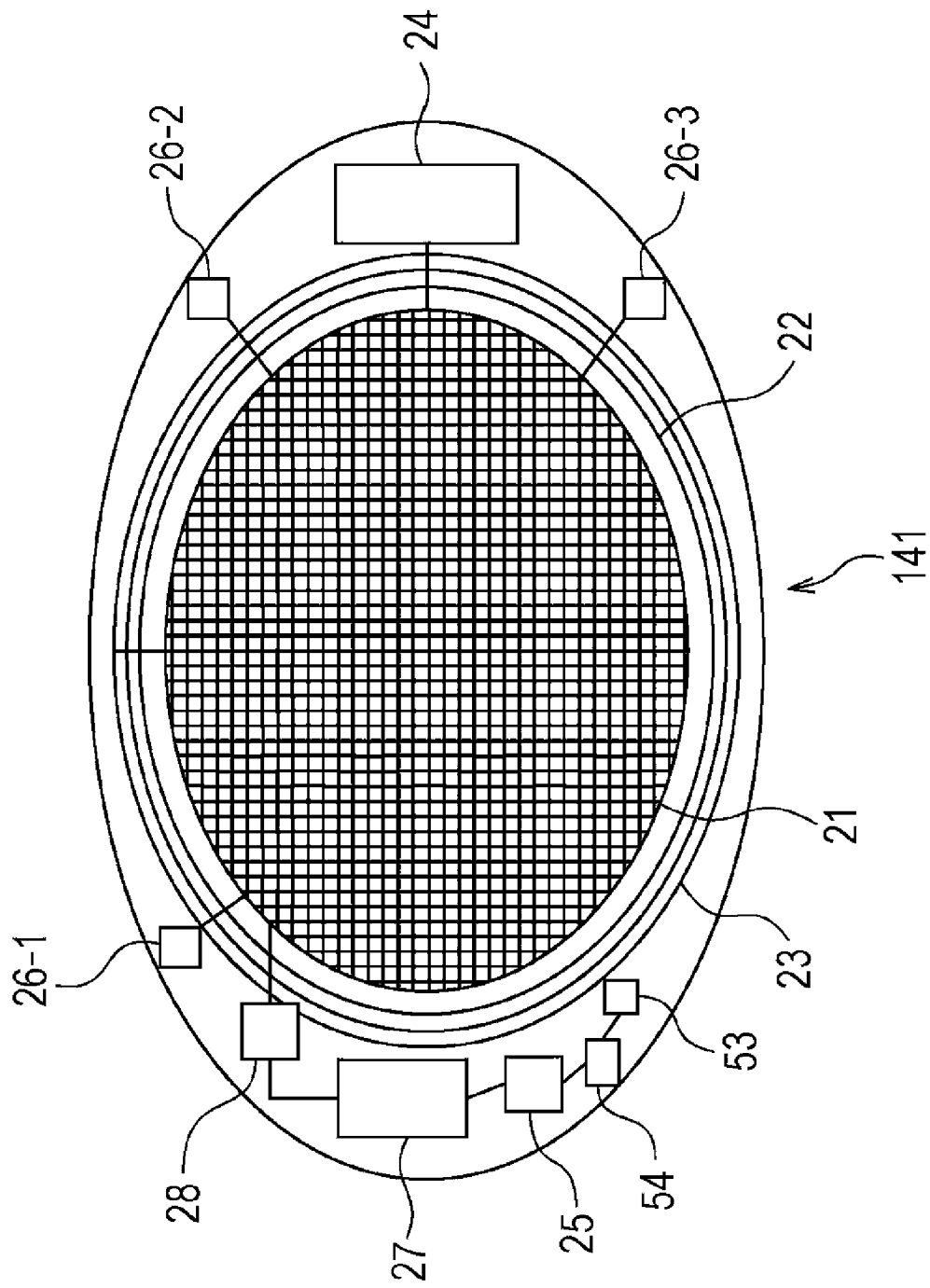
FIG. 19 is a diagram illustrating another configuration example of the display device.

In such a case, the display device is configured as illustrated in FIG. 19, for example. Note that, in FIG. 19, portions corresponding to those of the cases in FIG. 2 or 3 are assigned the same reference numerals, and description thereof will be omitted as appropriate.

A contact lens type display device display device 141 illustrated in FIG. 19 includes the display region 21, the electrical supply antenna 22, the signal antenna 23, the electrical generation unit 24, the posture detection unit 25, the tear detection unit 26-1 to the tear detection unit 26-3, the signal processing unit 27, the display element drive unit 28, the light emitting element 53, and the light receiving element 54.

The display device 141 is oval-shaped; however, the positional relationships between the display region 21 to the display element drive unit 28 and the operations thereof are the same as those of the case in FIG. 2. However, while the display pixels 51 and the light receiving elements 52 are provided in the display region 21 of the display device 141, the light emitting element 53 and the light receiving element 54 are not.

In the display device 141, the light emitting element 53 and the light receiving element 54 are provided on the bottom left portion in the drawing, that is, on a portion in the proximity of the outer circumference of the display device 141. In this case, the light emitting element 53 outputs the light for eyelid open-close detection toward the front side in the drawing, that is, toward the outside. Therefore, when the eyelid of the user is closed, since the light that is output from the light emitting element 53 is reflected by the underside of the eyelid and is incident on the light receiving element 54, the light receiving element 54 receives the light that is incident thereon, subjects the light to photoelectric conversion, and supplies the received light signal that is obtained as a result to the signal processing unit 27.

<Functional Configuration Example of Display Device>

Figure 20:
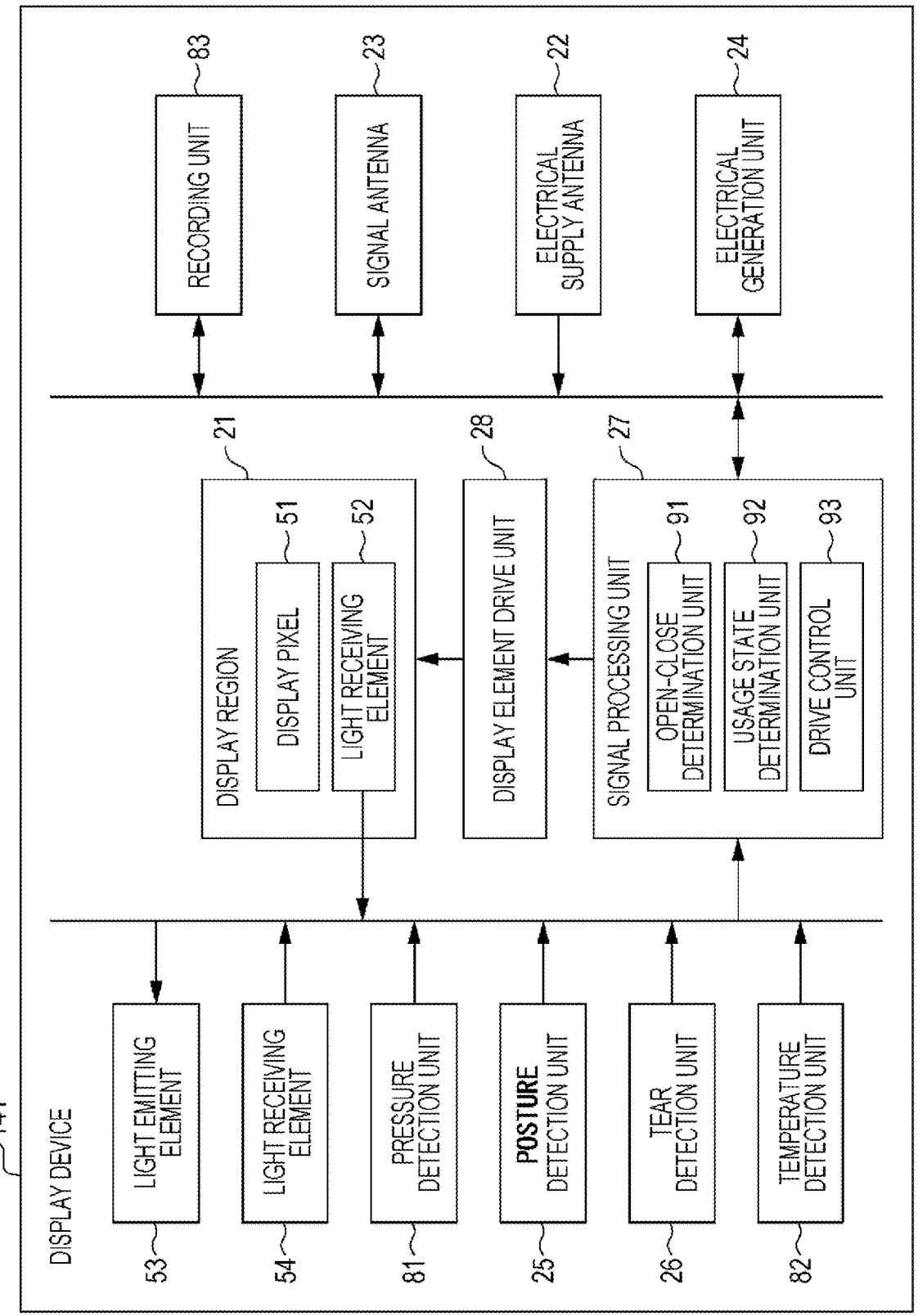
FIG. 20 is a diagram illustrating another functional configuration example of the display device.

The functional configuration of the display device 141 is assumed to be the configuration illustrated in FIG. 20, for example. Note that, in FIG. 20, portions corresponding to those of the case in FIG. 6 are assigned the same reference numerals, and description thereof will be omitted as appropriate.

The configuration of the display device 141 illustrated in FIG. 20 differs from the configuration of the display device 11 in that the light emitting element 53 and the light receiving element 54 are not provided in the display region 21, and the light emitting element 53 and the light receiving element 54 are provided outside of the display region 21. The other configuration is the same as that of the display device 11.

Therefore, in the display device 141, the driving of the light emitting element 53 is directly controlled by the drive control unit 93 of the signal processing unit 27, and the received light signal from the light receiving element 54 is supplied directly to the signal processing unit 27.

Modification Example 1 of Second Embodiment

<Configuration Example of Contact Lens Type Display Device>

Figure 21:
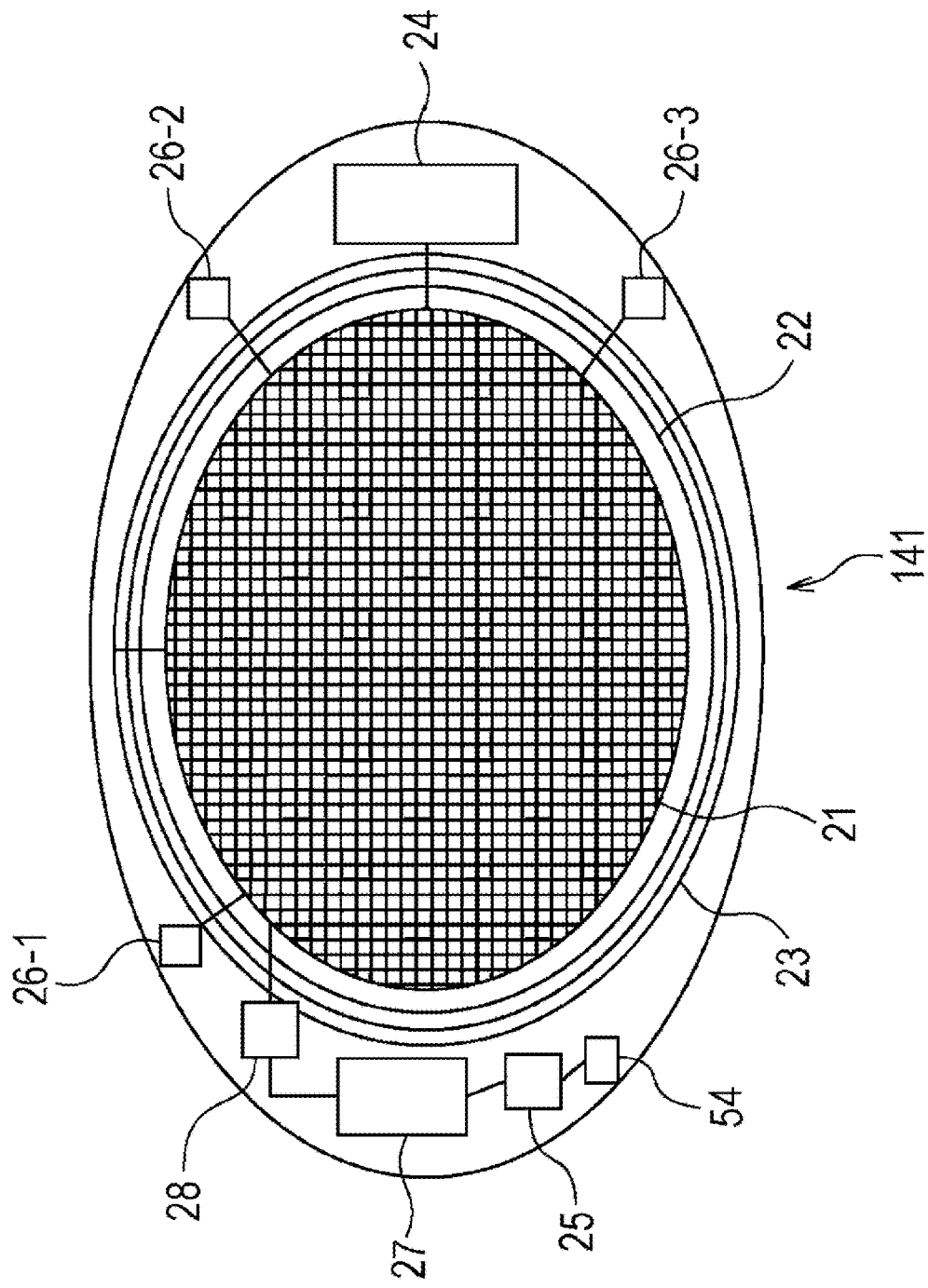
FIG. 21 is a diagram illustrating another configuration example of the display device.

Furthermore, an example is described in which the light emitting elements 53 and the light receiving elements 54 are provided on the outside of the display region 21 in the display device 141; however, as illustrated in FIG. 21, for example, only the light receiving element 54 may be provided without providing the light emitting element 53. Note that, in FIG. 21, portions corresponding to those of the case in FIG. 19 are assigned the same reference numerals, and description thereof will be omitted as appropriate.

In the display device 141 illustrated in FIG. 21, the light receiving element 54 for eyelid open-close detection is provided on a portion of the bottom left in the drawing; however, the light emitting element 53 for eyelid open-close detection is not. Therefore, in this example, the light receiving element 54 receives the light that is incident from the outside, and in the open-close determination unit 91, the open-close determination of the eyelid is performed based on the amount of light that is received from the outside by the light receiving element 54.

Modification Example 2 of Second Embodiment

<Configuration Example of Contact Lens Type Display Device>

Figure 22:
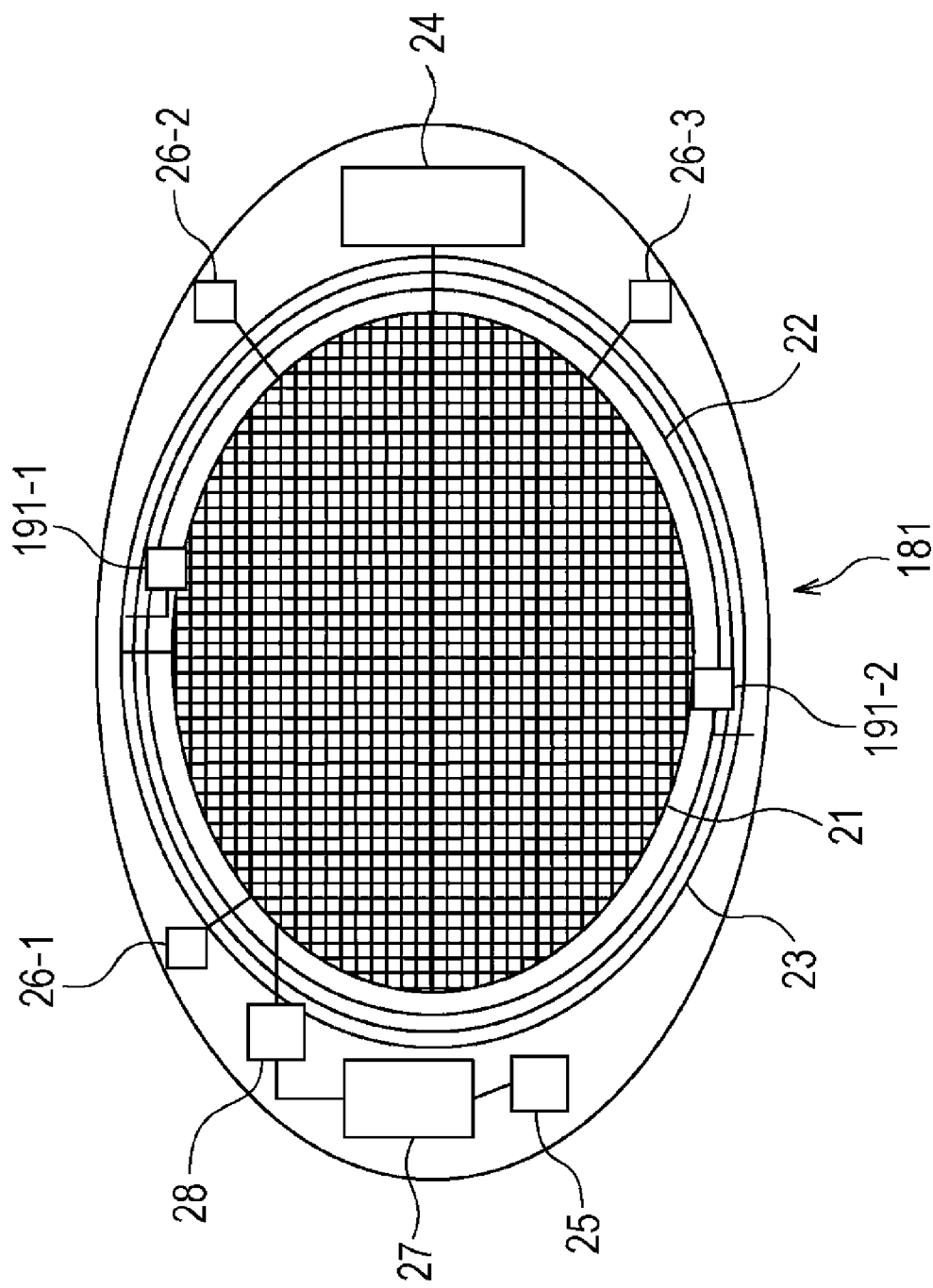
FIG. 22 is a diagram illustrating another configuration example of the display device.

When the light emitting element for eyelid open-close detection is not provided in the display device and only the light receiving element for eyelid open-close detection is provided, the display device may be configured as illustrated in FIG. 22, for example. Note that, in FIG. 22, portions corresponding to those of the case in FIG. 19 are assigned the same reference numerals, and description thereof will be omitted as appropriate.

A contact lens type display device display device 181 illustrated in FIG. 22 includes the display region 21, the electrical supply antenna 22, the signal antenna 23, the electrical generation unit 24, the posture detection unit 25, the tear detection unit 26-1, the tear detection unit 26-2, the tear detection unit 26-3, the signal processing unit 27, the display element drive unit 28, a light receiving element 191-1 and a light receiving element 191-2.

In the display device 181, the light receiving element 191-1 and the light receiving element 191-2 are respectively provided on a portion of the center-top side and a portion of the center-bottom side in the drawing of the display device 181. The light receiving element 191-1 and the light receiving element 191-2 are each provided on a portion in the proximity of the outer circumference of the display device 181 and on a portion of the outside.

The light receiving element 191-1 and the light receiving element 191-2 receive the light that is incident from the outside and supply received light signals which correspond to the amount of light that is received to the signal processing unit 27. Therefore, in the open-close determination unit 91 of the signal processing unit 27, the open-close determination of the eyelid is performed based on the amount of light that is received by the light receiving element 191-1 or the light receiving element 191-2 from the outside.

Note that, here, description is given of an example in which the two light receiving elements 191-1 and 191-2 are provided; however three or more light receiving elements for eyelid open-close detection may be provided.

Modification Example 3 of Second Embodiment

<Configuration Example of Contact Lens Type Display Device>

Figure 23:
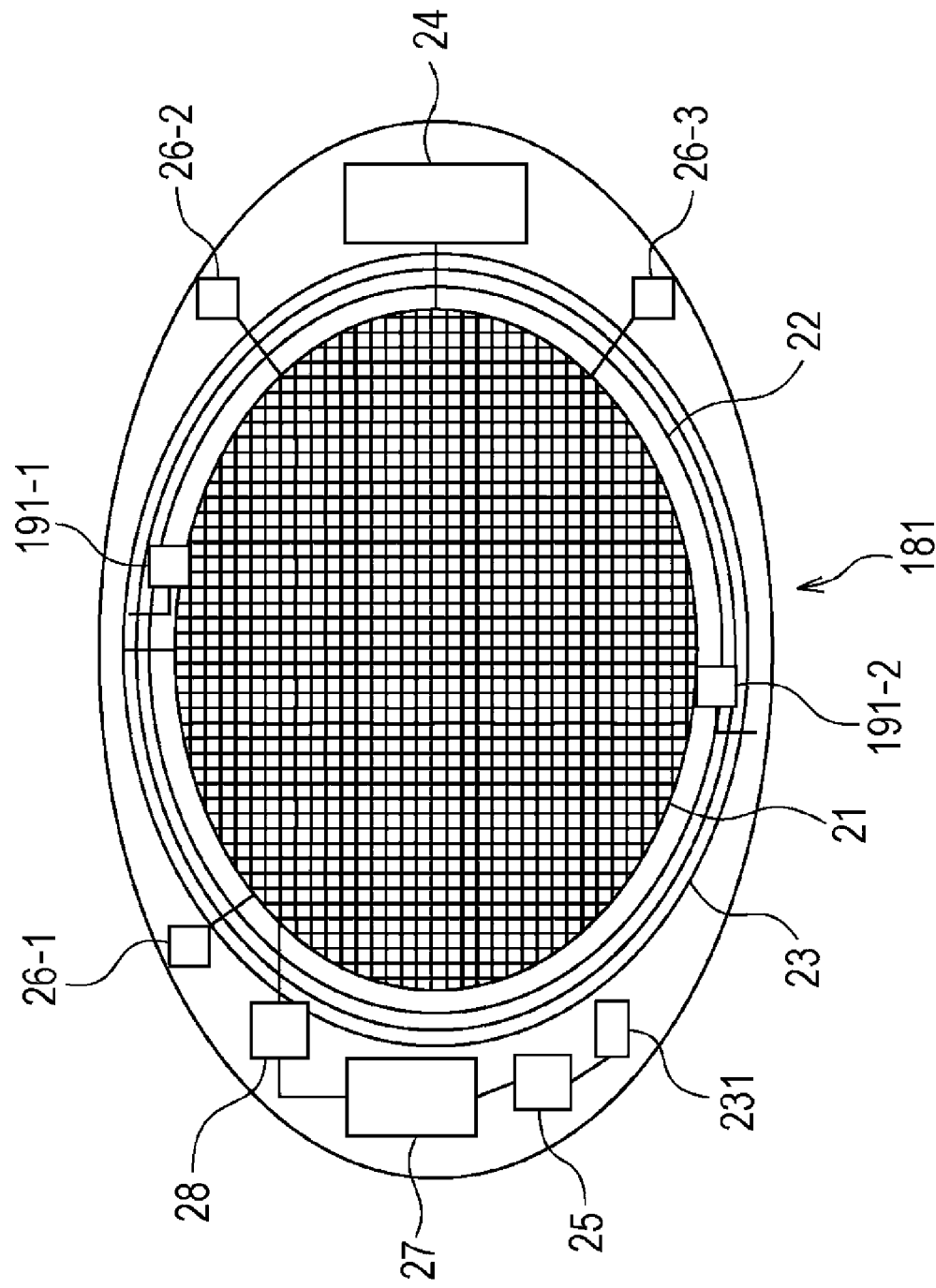
FIG. 23 is a diagram illustrating another configuration example of the display device.

As described above, a vibration unit which applies a stimulus to the eyeball of the user and promotes the generation of tears may be provided in the display device. In such a case, the display device is configured as illustrated in FIG. 23, for example. Note that, in FIG. 23, portions corresponding to those of the case in FIG. 22 are assigned the same reference numerals, and description thereof will be omitted as appropriate.

The contact lens type display device 181 illustrated in FIG. 23 is configured by further providing a vibration unit 231 to the display device 181 illustrated in FIG. 22.

For example, the vibration unit 231 is formed of a small motor, a piezoelectric element, or the like, applies an appropriate stimulus to the eyeball of the user by vibrating according to the control of the drive control unit 93, and promotes the generation (excretion) of tears of the user. For example, the drive control unit 93 drives the vibration unit 231 when it is detected that the eyeball of the user is dry as described above.

Note that, in the above description, it is described that the pressure detection unit 81, the posture detection unit 25, the tear detection unit 26, and the temperature detection unit 82 are provided in the display device 11 or the like; however, the pressure detection unit 81, the temperature detection unit 82, and the like are not necessarily all provided, and only the necessary parts may be provided. A configuration may be adopted in which the display region 21 is not provided in the display device 11 or the like, that is, a configuration without a display function.

In the above description, description is given of an example of a case in which the display device described in each of the embodiments of the display device 11 or the like is mounted to a human; however, as long as the living body has an eyelid and an eyeball, the display device may be used on any type of living body and is not limited to humans.

Incidentally, the series of processes that is described above can be executed using hardware and can be executed using software. When the series of processes is executed using software, the program which forms the software is installed on the display device 11 or the like, for example.

For example, in the display device 11, the series of processes described above are performed by the signal processing unit 27 loading the program that is recorded in the recording unit 83 into a memory (not shown) and executing the program.

It is possible to provide the program to be executed by the display device 11 or the like via a wired or wireless transmission medium such as a local area network, the Internet, or a digital satellite broadcast.

Note that, the program to be executed by the display device 11 may be a program in which the processes are performed in time series in the order described in the present specification. The program may also be a program in which the processes are performed in parallel or at the necessary timing such as when the process is called.

The embodiments of the present technology are not limited to the embodiment described above, and various modifications may be made within a scope not departing from the main concept of the present technology.

For example, in the present technology, it is possible to adopt a cloud computing configuration in which one function is distributed, shared and processed by a plurality of devices via a network.

In addition to executing each of the steps described in the flowcharts described above using one device, it is possible to distribute and execute the steps over a plurality of devices.

Furthermore, when a plurality of processes are contained in one step, in addition to executing the processes on one device, it is possible to distribute and execute the plurality of processes contained in that one step on a plurality of devices.

The effects described in the present specification are merely exemplary, are not limited, and other effects may be present.

The present technology can adopt the following configurations.

(1) A device configured to be placed in contact with an eye of a user, the device comprising:
at least one detector configured to measure at least one property; and
a signal processor configured to determine, based on the at least one property, whether
the eye of the user is closed.
(2) The device according to (1), further comprising:
a display configured to display information to the eye of the user.
(3) The device according to (2), wherein the display is located in a center portion of the device.
(4) The device according to (3), wherein the at least one detector and the signal processor are located in a periphery portion of the device.
(5) The device according to any of the previous configurations, wherein the device is a contact lens device.
(6) The device according to any of the previous configurations, wherein the signal processor is further configured to determine whether the user is sleeping.
(7) The device according to any of the previous configurations, wherein the at least one detector comprises a light detector configured to detect an amount of light received.
(8) The device according to (7), wherein the light detector is configured to detect an amount of light received from outside the device.
(9) The device according to (7), wherein the light detector is configured to detect an amount of light received from a light emitting element of the device.
(10) The device according to any of the previous configurations, wherein:
the at least one detector comprises a temperature detector configured to detect a temperature outside the device; and
the signal processor determines whether the eye of the user is closed based on the temperature detected by the temperature detector.

(11) The device according to (10), wherein the signal processor determines whether the eye of the user is closed based on a change in temperature detected by the temperature detector.
(12) The device according to any of the previous configurations, wherein:
the temperature detector is further configured to detect a temperature of the eye of the user; and
the signal processor determines whether the eye of the user is closed based on the temperature outside the device detected by the temperature detector and the temperature of the eye of the user detected by the temperature detector.
(13) The device according to any of the previous configurations, wherein:
the at least one detector comprises a pressure detector configured to detect a pressure applied to the device; and
the signal processor determines whether the eye of the user is closed based on the pressure detected by the pressure detector.
(14) The device according to any of the previous configurations, wherein the signal processor is further configured to determine a number of blinks made by the user.
(15) The device according to any of the previous configurations, further comprising a light emitter for irradiating an eyelid of the user with light, wherein the at least one detector comprises a light detector configured to detect an amount of light from the light emitter that is reflected by the eyelid.
(16) The device according to (15), wherein the signal processor is further configured to determine pulse information and/or blood flow information of the user based on the amount of light detected by the light detector.
(17) The device according to (16), wherein the signal processor is further configured to determine whether the user is sleeping based on the pulse information and/or the blood flow information of the user.
(18) The device according to any of the previous configurations, further comprising a stimulator configured to stimulate the user to form tears using light and/or vibration.
(19) The device according to any of the previous configurations, wherein:
the at least one detection comprises a tear detector configured to detect an amount of tears and/or an amount of a particular component of the tears;
the signal processor is further configured to determine a state of the user based on the amount of tears and/or the amount of the particular component of the tears detected by the tear detector.
(20) The device according to (19), wherein the tear detector is located on the device such that, when the device is worn by the user, the tear detector is nearer to a tear gland of the user than other components of the device.
(21) The device according to any of the previous configurations, wherein:
the at least one detection comprises a posture detector configured to detect posture and/or movement of the head of the user;
the signal processor is further configured to determine a state of the user based on the posture and/or the movement of the head of the user detected by the posture detector.
(22) The device according to (21), wherein the posture detector comprises a gyroscope and/or an accelerometer.
(23) A device configured to be placed in contact with an eye of a user, the device comprising:
a temperature detector configured to detect a temperature outside the device and/or a temperature of the eye of the user.
(24) A detection device capable of being mounted to an eyeball, including an eyelid open-close detection unit which detects opening and closing of an eyelid of a living body, in a state of being mounted to the eyeball, based on at least one of an amount of light that is incident from an outside of the detection device, a pressure that is applied to the detection device, and living body information that is obtained from the living body to which the detection device is mounted.
(25) The detection device according to (24), further including a display control unit which controls display of an image according to detection results of the opening and closing of the eyelid.
(26) The detection device according to (24) or (25), further including a light receiving element which receives light that is incident from the outside, in which the eyelid open-close detection unit detects the opening and closing of the eyelid based on an amount of light that is received by the light receiving element.
(27) The detection device according to (24) or (25), further including a light emitting element which outputs light toward the outside, and a light receiving element which receives the light that is output from the light emitting element and is reflected by the eyelid, in which the eyelid open-close detection unit detects the opening and closing of the eyelid based on an amount of light that is received by the light receiving element.
(28) The detection device according to (24) or (25), further including a pressure detection unit which detects a pressure that is applied to the detection device, in which the eyelid open-close detection unit detects the opening and closing of the eyelid based on the pressure that is detected by the pressure detection unit.
(29) The detection device according to (24) or (25), further including a temperature detection unit which detects a temperature of the outside of the detection device as the living body information, in which the eyelid open-close detection unit detects the opening and closing of the eyelid based on the temperature that is detected by the temperature detection unit.
(30) The detection device according to (29), in which the eyelid open-close detection unit detects the opening and closing of the eyelid based on a change in the temperature of the outside of the detection device.
(31) The detection device according to (29) or (30), in which the temperature detection unit further detects a temperature of the eyeball side of the detection device, and wherein the detection device further includes a usage state determination unit which determines whether or not the living body is in a sleeping state based on the temperature of the outside and the temperature of the eyeball side of the detection device.
(32) The detection device according to any one of (24) to (29), further including a usage state determination unit which determines whether or not the living body is in a sleeping state based on information relating to the living body.
(33) The detection device according to (32), further including a calculation unit which calculates a number of blinks based on a detection result of the opening and closing of the eyelid, in which the usage state determination unit determines whether or not the living body is in the sleeping state based on the number of blinks.

(34) The detection device according to (32), further including a calculation unit which calculates pulse information or blood flow information of the living body based on an amount of light that is received, which is the light with which the eyelid is irradiated and which is reflected by the eyelid, or based on a pressure that is applied to the detection device, in which the usage state determination unit determines whether or not the living body is in the sleeping state based on the pulse information or the blood flow information.

(35) The detection device according to (32), further including a posture detection unit which detects a posture of the living body, in which the usage state determination unit determines whether or not the living body is in the sleeping state based on results of the posture detection.

(36) The detection device according to (32), further including a tear detection unit which detects a tear excretion amount of the living body, in which the usage state determination unit determines whether or not the living body is in the sleeping state based on the tear excretion amount.

(37) The detection device according to (26), in which the tear detection unit is provided to be positioned in a proximity of a tear gland of the living body in a state in which the detection device is mounted to the eyeball.

(38) The detection device according to any one of (32) to (37), in which the usage state determination unit determines whether or not the living body is in the sleeping state based on information relating to the living body and detection results of the opening and closing of the eyelid.

(39) The detection device according to any one of (24) to (38), further including a stimulation unit which stimulates the eyeball using light or vibration and promotes generation of tears of the living body.

(40) The detection device according to any one of (24) to (39), further including a tear component analysis unit which performs component analysis of tears that are excreted from the living body, and a living body state determination unit which determines a state of the living body using at least results of the component analysis of the tears.

(41) The detection device according to any one of (24) to (40), in which the detection device is a contact lens type device.

(42) A detection method of a detection device capable of being mounted to an eyeball, the method including a step of detecting opening and closing of an eyelid of a living body, in a state in which the detection device is mounted to the eyeball, based on at least one of an amount of light that is incident from an outside of the detection device, a pressure that is applied to the detection device, and living body information that is obtained from the living body to which the detection device is mounted.

(43) A program which causes a computer controlling a detection device capable of being mounted to an eyeball to execute a process including a step of detecting opening and closing of an eyelid of a living body, in a state in which the detection device is mounted to the eyeball, based on at least one of an amount of light that is incident from an outside of the detection device, a pressure that is applied to the detection device, and living body information that is obtained from the living body to which the detection device is mounted.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

11 Display device
21 Display region
25 Posture detection unit
26-1 to 26-3, 26 Tear detection unit
27 Signal processing unit
51-1 to 51-5, 51 Display pixel
52-1 to 52-5, 52 Light receiving element
53-1, 53-2, 53 Light emitting element
54-1, 54-2, 54 Light receiving element
81 Pressure detection unit
82 Temperature detection unit
91 Open-close determination unit
92 Usage state determination unit
93 Drive control unit
231 Vibration unit

The invention claimed is:

1. A device configured to be placed in contact with an eyeball of an eye of a user, the device comprising:
   a lens structured to be placed adjacent the eyeball of the user;
   a display region disposed in a first portion of the lens; and
   electronic circuitry disposed in a second portion of the lens,
   wherein the display region is comprised of:
      first emitter pixels that emit a first light toward the eyeball of the user, the first light having a first predetermined wavelength shorter than 805 nm,
      first receiver pixels that receive light of the first predetermined wavelength directly reflected from inside the eyeball of the user,
      second emitter pixels that emit a second light away from the eyeball of the user and toward an eyelid of the user, the second light having a second predetermined wavelength different from the first predetermined wavelength, the second predetermined wavelength being longer than 805 nm, and
      second receiver pixels that receive light of the second predetermined wavelength emitted from the second emitter pixels and reflected by the eyelid of the user, and
   wherein the electronic circuitry is comprised of:
      at least one detector that measures at least one property, and
      a signal processor that:
         determines, based on one or more of the at least one property, whether the eye of the user is closed, and
         determines a line of sight of the eyeball of the user based on a location of a region of the first receiver pixels, in which an amount of the light of the first predetermined wavelength received by the region of the first receiver pixels is different from an amount of the light of the first predetermined wavelength received by another region of the first receiver pixels.

2. The device according to claim 1, wherein the first emitter pixels are comprised of display pixels that display information to the eyeball of the user.

3. The device according to claim 2, wherein the display region is located in a center portion of the lens.

4. The device according to claim 3, wherein the electronic circuitry is located in a periphery portion of the lens.

5. The device according to claim 1, wherein the device is a contact lens device.

6. The device according to claim 1, wherein the signal processor determines whether the user is sleeping.

7. The device according to claim 1, wherein the display region is further comprised of second pixels that receive external light.

8. The device according to claim 7, wherein the second pixels detect an amount of the external light received from outside the eye of the user.

9. The device according to claim 1, wherein:
the at least one detector is comprised of a temperature detector that detects a temperature outside the device, and
the signal processor determines whether the eye of the user is closed based on the temperature detected by the temperature detector.

10. The device according to claim 9, wherein the signal processor determines whether the eye of the user is closed based on a change in temperature detected by the temperature detector.

11. The device according to claim 9, wherein:
the temperature detector detects a temperature of the eyeball of the user, and
the signal processor determines whether the eye of the user is closed based on the temperature outside the device detected by the temperature detector and the temperature of the eyeball of the user detected by the temperature detector.

12. The device according to claim 1, wherein:
the at least one detector is comprised of a pressure detector that detects a pressure applied to the device, and
the signal processor determines whether the eye of the user is closed based on the pressure detected by the pressure detector.

13. The device according to claim 1, wherein the signal processor determines a number of blinks made by the eye of the user.

14. The device according to claim 1, wherein the signal processor determines, based on an amount of light received by the first receiver pixels, pulse information of the user, or blood flow information of the user, or pulse information and blood flow information of the user.

15. The device according to claim 14, wherein the signal processor determines whether the user is sleeping based on the pulse information of the user, or the blood flow information of the user, or the pulse information and the blood flow information of the user.

16. The device according to claim 1, wherein the signal processor causes an emitter pixel of the first emitter pixels of the display region or a vibration circuit of the electronic circuitry to apply a stimulus to the eye of the user to cause tears to form.

17. The device according to claim 1, wherein:
the at least one detector is comprised of a tear detector that detects an amount of tears, or an amount of a particular component of tears, or an amount of tears and an amount of a particular component of tears, and
the signal processor determines a state of the user based on the amount of tears, or the amount of the particular component of tears, or the amount of tears and the amount of the particular component of tears detected by the tear detector.

18. The device according to claim 17, wherein the tear detector is located on the lens such that, when the device is worn by the user, the tear detector is nearer to a tear gland of the user than a nearness of other components of the device to the tear gland of the user.

19. The device according to claim 1, wherein:
the at least one detector is comprised of a gyroscope, or an accelerometer, or a gyroscope and an accelerometer to detect a posture of the user, or a head movement of the user, or a posture and a head movement of the user, and
the signal processor determines a state of the user based on the posture of the user, or the head movement of the user, or the posture and the head movement of the user detected by the gyroscope, or the accelerometer, or the gyroscope and the accelerometer.

20. The device according to claim 1, wherein the first emitter pixels and the second emitter pixels alternately emit the light of the first predetermined wavelength and the light of the second predetermined wavelength.

21. The device according to claim 1, wherein the first emitter pixels and the second emitter pixels emit at a same time the light of the first predetermined wavelength and the light of the second predetermined wavelength.

* * * * *